(12) United States Patent
Hirabayashi et al.

(10) Patent No.: US 6,348,347 B1
(45) Date of Patent: Feb. 19, 2002

(54) FINE ALGAE CULTURE DEVICE

(75) Inventors: Seishiro Hirabayashi, Mishima (JP); Alexander Prilutsky, Beer Sheva (IL); Hisato Sadamatsu, Kawasaki (JP)

(73) Assignee: Micro Gaia Co., Ltd., Numazu (JP)

( * ) Notice: Subject to any disclaimer, the term of this patent is extended or adjusted under 35 U.S.C. 154(b) by 0 days.

(21) Appl. No.: 09/424,707

(22) PCT Filed: Mar. 29, 1999

(86) PCT No.: PCT/JP99/01585

§ 371 Date: Feb. 17, 2000

§ 102(e) Date: Feb. 17, 2000

(87) PCT Pub. No.: WO99/50384

PCT Pub. Date: Oct. 7, 1999

(30) Foreign Application Priority Data

Mar. 31, 1998 (JP) .......................... 10-086558
Jun. 17, 1998 (JP) .......................... 10-169403

(51) Int. Cl.[7] ................................. C12M 1/04
(52) U.S. Cl. .................. 435/292.1; 435/296.1; 47/1.4; 261/121.1; 239/229; 239/231
(58) Field of Search ................ 435/257.1, 257.3, 435/292.1, 296.1; 47/1.4; 210/220; 261/121.1, 123, 124; 239/722, 754, 263, 264, 229, 233

(56) References Cited

U.S. PATENT DOCUMENTS 3,224,143 A * 12/1965 Tew et al.
4,324,068 A * 4/1982 Anthony
4,952,511 A * 8/1990 Radmer
5,534,417 A * 7/1996 Arad et al.
5,958,761 A * 9/1999 Yogev et al.

FOREIGN PATENT DOCUMENTS

JP 8-38156 A * 2/1996
JP 8-116960 A * 5/1996

* cited by examiner

Primary Examiner—William H. Beisner
(74) Attorney, Agent, or Firm—Armstrong, Westerman, Hattori, McLeland & Naughton, LLP

(57) ABSTRACT

This invention relates to a culture device of a domed shape, a conical shape, or a cylindrical shape of a closed type used for culture of microalgae, and a gas discharge device set so as to be movable in the culture device. The culture device is basically composed of a transparent inside member (a semi-spherical dome, a conical peripheral wall, or a cylindrical peripheral wall), a transparent outside member, and a bottom portion connecting the lower ends of the two members, a cylindrical opening portion is provided at the top part of the outside member, and a gas introducing member and a discharging member of a culture solution are provided in the bottom portion. The gas discharge device is basically composed of two opposed rectangular base plates, a bubble guide member, and a discharge nozzle. The culture solution can be agitated without mechanical agitation and the culture can be carried out in high concentrations.

18 Claims, 15 Drawing Sheets

FINE ALGAE CULTURE DEVICE

TECHNICAL FIELD

The present invention relates to a culture device of a domed shape, a conical shape, or a cylindrical shape used in culture of photosynthetic organisms such as microalgae or the like, a gas discharge device disposed so as to be movable in the culture device and functioning to supply gas necessary for the culture into a culture solution and agitate the culture solution, or a culture system as a combination of the culture device with the gas discharge device.

BACKGROUND ART

In order to produce useful substances such as vitamins, amino acids, pigments, proteins, polysaccharides, fatty acids, and so on or in order to dispose of carbon dioxide which is considered to be one of causes of global warming, extensive research has been conducted heretofore on mass culture of microorganisms including microalgae such as Chlorella, Spirulina, or the like, and products of cultures based on the result of research are commercially available.

Most of the algae among these microorganisms absorb carbon dioxide to biosynthesize the useful substances by photosynthesis. In this case, because it is important to effect the culture of algae efficiently, a culture apparatus for making the algae efficiently perform the photosynthesis is necessary. Therefore, improvement in the conventional culture apparatus and development of new culture apparatus are under way.

The conventional algae culture apparatus commonly known include, for example, culture ponds, raceway culture devices, tubular culture devices, liquid membrane forming culture devices, and so on. The artificial culture ponds are of a type in which a culture pool or a culture tank is constructed, for example, of concrete outdoors, the culture solution is poured into the pool to form a culture pond, and the microalgae such as Chlorella or the like are cultured in the solution by making use of the sunlight. However, the systems of this type necessitate the surface area of the pool, for example, of 3000 $M^2$ and are thus normally huge.

In addition, when the microalgae are cultured in the system of this type, concentrations of the microalgae increase in the culture solution with progress of culture, so as to turn the solution into deep green and thus inhibit the sunlight from reaching the bottom part of the culture pond. From this phenomenon, there will arise a problem that the overall efficiency of photosynthesis of algae is decreased, unless the culture concentrations of the microalgae are lowered.

For this reason, the depth of the solution has to be kept below 15 cm and broad areas are necessary for the volume culture of microalgae. Since the concentrations of the culture solution cannot be high, there arises a problem that, for collecting the cultures from the solution, the cultures must be collected from an enormous amount of the culture solution with low concentration.

On the other hand, the culture ponds have to be agitated to facilitate the photosynthesis of the microalgae, but a lot of energy is necessary for agitating the huge amount of the solution of low concentration. Further, because the culture ponds are set outdoors and are open to the air, impurities of dirt, dust, etc. are mixed readily into the solution, and microorganisms and other algae floating in the air are mixed into the ponds to propagate; these pose another problem that the cultures cannot be obtained in high purity and with high quality.

Since the culture ponds are set outdoors, the temperature varies with variations in climate and it is thus very difficult to keep the temperature of the ponds constant. Particularly, the culture ponds have such a drawback that the temperature becomes too low in the winter season, depending upon regions.

For these reasons, the culture of algae making use of the culture ponds has such a drawback that it cannot be applied to the algae except for those such as Chlorella, Spirulina, and Dunaliella which can grow even under such a special condition as high pH or high salinity.

The raceway culture apparatus is constructed in such structure that the inside of a culture tank is partitioned with straightening plates to form a circuit path of the culture solution and the algae are cultivated by a method for circulating the culture solution in the circuit path by circulating means. This method is an improvement in the method of the culture ponds, but it also fails to utilize the light efficiently, because rates of photosynthesis of algae are lowered with progress of the culture, as in the case of the culture method with the culture ponds. This also raises a problem of low utilization efficiency of carbonic acid gas. For accomplishing efficient utilization of light, there is also a suggestion of guiding the sunlight through optical fibers into the solution. (Japanese Laid-open Utility Model Application No. 5-43900)

However, since the solution is circulated by mechanical agitation in the case of the culture of algae by this method, this method will encounter such an inevitable drawback that cells of algae are subject to breakage or shear stress (a phenomenon in which the algae are cut by shearing stress to degrade the activity of cells and thus make growth rates slower).

The tubular culture apparatus is an apparatus for culturing the microalgae etc. by use of the culture tank constructed of a light-transmitting tube. When the algae are cultured by use of this apparatus, there is no contamination of the culture solution due to various germs or the like and the culture concentrations can also be high; therefore, this is an extremely advantageous method for separating the algae from the culture solution and collecting the useful substances produced by the algae.

However, after long-term culture of algae, the algae attach to the internal wall of the tube, so as to considerably decrease the quantity of light transmitted by the tube. This phenomenon makes the efficient culture of microalgae difficult and it is not easy to remove the algae attaching to the internal wall of the tube.

For solving this problem, there is a suggestion about a method for putting cleaning balls in the tube and always circulating these balls with the culture solution, thereby cleaning the internal wall of the tube (Japanese Laid-open Patent Application No. 6-90739). This method, however, has many problems; it is not possible to continuously remove the dirt and the attachment of algae on the internal wall of the tube well, the balls have to be collected and cleaned, the balls always have to be circulated in the tube, and so on. A further problem of the culture of algae according to this method is that oxygen gas resulting from the photosynthesis of algae stays inside the tube because of the culture inside the tube and this oxygen acts to inhibit the photosynthesis of algae conversely (inhibition of photosynthesis). There is thus another suggestion about an idea of a device for suppressing the adverse effect on the culture due to the oxygen evolving in the photosynthesis. (Japanese Laid-open Patent Application No. 9-121835)

The liquid film forming culture apparatus is one constructed in such structure that a light-transmitting domed lid is placed on the culture tank, the culture solution is sprayed from below toward the internal surface at the top of the domed lid to form a liquid film of the culture solution on the internal surface of the lid, and this liquid film is exposed to the light. (Japanese Laid-open Patent Application No. 8-38159)

This suggested method, however, has problems that it requires a circulating pump for continuously forming the liquid film, that it is not suitable for the mass culture, that the sunlight cannot be utilized, and so on.

Since the microalgae accumulate the useful substances in their body through the photosynthesis, a significant challenge is to make the microalgae conduct the photosynthesis at as high efficiency as possible. Conceivable factors for the efficient photosynthesis are enlargement of the light-receiving area of the culture apparatus, efficient agitation of the culture solution, adjustment of the thickness or the depth of the culture solution, easiness of cleaning to remove the microalgae attaching to the internal surface of the culture apparatus, control of temperature, prevention of mixture of foreign germs, other microalgae, and impurities, and so on.

The issue of the light-receiving area is influenced by how large the light-receiving area is or by how efficiently the culture solution is exposed to the light.

For example, in the case of the culture tanks or the culture ponds, the surface area is determined by the surface of the culture tanks or the culture ponds; therefore, the enlargement of the surface area can be achieved only by increasing the size of the tanks or the ponds and there is no alternative means.

The agitation of the culture solution is essential to uniform irradiation of light to the culture solution and an ordinary means therefor is often agitation or movement of the solution, for example, by a pump, or mechanical agitation in the tanks, the ponds, and so on.

Such mechanical agitation, however, is not preferable, because it causes breakage or shear stress of cells of microalgae.

Since photosynthesis rates differ depending upon kinds of microalgae, it is necessary to employ different depths of the culture solution between algae of low rates and algae of high rates. It is also necessary to change the depth according to an expected culture concentration. As described, the thickness or depth of the culture solution needs to be freely adjusted according to the conditions including the kind of microalgae, the expected culture concentration, and so on.

The removal and cleaning of the microalgae attaching to the internal surface of the culture apparatus is not so significant in the case of the open type culture ponds and culture tanks set outdoors. This removal and cleaning is, however, essential to the culture apparatus of the closed type, because the attaching microalgae come to intercept the light. In addition, the apparatus needs to be constructed in such structure that at the stage of completion of the culture the inside surface of the apparatus can be cleaned for the next culture, so as to remove the attachments readily.

The temperature control is very important, particularly, for the closed type apparatus, because the temperature of the solution becomes too high in the summer season and causes a trouble in the culture. One of solutions to it is a method for mixing cool water into the culture solution, but, because of dilution of the culture solution, a large amount of the culture solution thus diluted has to be dealt with in the next step of collection of the cultured algae. This method is, therefore, very disadvantageous from the industrial aspect.

The culture devices are normally either those for outdoor use or those for indoor use. Therefore, if the devices for outdoor use are used indoors, there will arise a problem that the efficiency of utilization of light is low; on the other hand, there also arises a problem that the devices for indoor use cannot be used outdoors. There are thus increasing demands for the culture apparatus of simple structure that permits the culture under ordinary culture conditions both indoors and outdoors.

The agitation of the culture solution is an essential operation to uniform culture. The reason is that it is carried out for the following purposes; (1) to cancel the difference of culture rates appearing between the surface layer part and the deep layer part of the liquid medium; (2) to uniformly distribute the gas such as air, carbon dioxide, or the like across the whole of the liquid medium or the culture solution; (3) to uniformly distribute the light over the microalgae to be cultured; (4) to prevent the microalgae likely to form colonies during the culture from settling and depositing in the liquid bottom part and to make them re-scattered in the culture solution; and so on.

It is thus necessary to always agitate the culture solution and to supply the necessary air or carbonic acid gas or the like into the culture solution.

An object of the present invention is, therefore, to provide a closed type culture device of microalgae as a culture device overcoming the drawbacks of the conventional open type or closed type culture devices, of which the shape is domed, conical, or cylindrical and which has the advantages including the following: (1) the foreign germs and impurities are prevented from being mixed in the device; (2) the temperature control of the culture solution is easy; (3) the solution can be agitated without mechanical agitation of the culture solution, so as to prevent the cells of algae from being broken and prevent the shear stress from appearing; (4) the culture concentrations can be set high; (5) the cleaning of the device is easy; (6) the culture is not inhibited by the evolving oxygen; and (7) the efficiency of utilization of light is high.

Another object of the present invention is to provide a gas discharge device used in the culture device, which has advantages including the following; when the necessary gas is supplied into the culture solution by use of this device, the device undergoes movement to agitate the solution and the solution is also agitated by the discharged gas, whereby contact is extremely good between the supplied gas and the culture solution, thereby increasing the culture efficiency.

Further, the present invention relates to a culture apparatus characterized by a combination of the above-stated culture device with the above-stated gas discharge device.

DISCLOSURE OF THE INVENTION

A culture device of microalgae according to the present invention is a culture device of either shape selected from a domed shape, a conical shape, and a cylindrical shape; the culture device of the domed shape is a culture device of a domed shape comprising an outside semispherical dome of a transparent material, an inside semispherical dome of a transparent material, and a bottom portion connecting lower ends of the two domes, wherein a cylindrical opening portion is provided at top part of the outside semispherical dome, and an introducing member of air and/or carbonic acid gas and a discharging member of a culture solution are provided in the bottom portion, and wherein a member for water sprinkling is provided outside the cylindrical opening portion and a sprinkled water receiver is provided around the outside periphery of the bottom portion as occasion may demand;

the culture device of the conical shape is a device comprising an outside conical peripheral wall of a transparent material, an inside conical peripheral wall of a transparent material, and a bottom portion connecting lower ends of the two peripheral walls, wherein a cylindrical opening portion is provided at top part of the outside conical peripheral wall, and an introducing member of air and/or carbonic acid gas and a discharging member of a culture solution are provided in the bottom portion, and wherein a member for water sprinkling is provided outside the cylindrical opening portion and a sprinkled water receiver is provided around the outside periphery of the bottom portion as occasion may demand;

the culture device of the cylindrical shape is a device comprising an outside cylindrical peripheral wall having an upper wall of a transparent material, an inside cylindrical peripheral wall having an upper wall of a transparent material, and a bottom portion connecting lower ends of the two peripheral walls, wherein a cylindrical opening portion is provided in central part of the upper wall of the outside cylindrical peripheral wall, and an introducing member of air and/or carbonic acid gas and a discharging member of a culture solution are provided in the bottom portion, and wherein a water sprinkling member is provided outside the cylindrical opening portion and a sprinkled water receiver is provided around the outside periphery of the bottom portion as occasion may demand.

A gas discharge device for use in the culture device of microalgae is a device comprising two opposed rectangular base plates, a bubble guide member of a U-shaped cross section or an inverted-U-shaped cross section opening down, and a discharge nozzle, wherein the bubble guide member is set as inclined with respect to upper surfaces of the rectangular base plates, an inclined wall as an upper surface thereof is bent at an upper end thereof to form an upper wall extending substantially horizontally, the bubble guide member has side walls hanging down from the both side edges of the inclined wall and upper wall, and lower ends of the two side walls are joined to the upper surfaces of the rectangular base plates, wherein the discharge nozzle is set through a through hole bored in a lower portion of the inclined wall so as to be rotatable, wherein at least one of the opposed rectangular base plates is bent in the same direction at a front end portion and/or at a rear end portion as occasion may demand, or wherein at least one of the rectangular base plates is provided with weight adjusting means.

Further, the present invention is a culture apparatus as a combination of the aforementioned culture device with the above gas discharge device.

The transparent material used in the culture devices can be any transparent material as long as it is excellent in the light-transmitting property and has sufficient weather resistance and resistance to ultraviolet rays; for example, it can be selected from materials such as acrylic resin, polycarbonate, polypropylene, polyethylene, polyvinyl chloride, glass, and so on; the synthetic resin can be suitably applicable in terms of ease to work; particularly, the acrylic resin is a most preferable material, because it has the aforementioned characteristics.

The gas introduced into the culture device must contain carbonic acid gas in its components and may be one with an increased concentration of carbonic acid gas by mixing carbonic acid gas in air; the air and carbonic acid gas may also be introduced separately into the device.

The carbonic acid gas is most preferably used in the form of a mixture with air. While an air bubble containing carbonic acid gas rises to the surface with agitating the culture solution, the carbonic acid gas is dispersed and absorbed in the culture solution and the air functions to remove oxygen evolving in the culture from the culture solution. If the carbonic acid gas is introduced alone into the culture solution introducing rates of carbonic acid gas will be low and dispersing rates of carbonic acid gas into the culture solution will tend to become slow inevitably.

The cylindrical opening portion works to exhaust the air introduced into the culture solution, unused carbonic acid gas, and evolving oxygen into the atmosphere; however, if the opening portion is open to the atmosphere, the impurities of dust etc. will enter the device. In order to prevent the mixture of such substances, it is preferable to provide the opening portion with a filter member or to provide the opening portion with such a lid member as to act in similar fashion to the filter member.

This opening portion may be molded in an integral form with the outside semispherical dome, the outside conical peripheral wall, or the upper wall of the outside cylindrical peripheral wall or may be one molded separately and fixed thereto.

The culture device of the domed shape, the conical shape, or the cylindrical shape used as a culture device body can be constructed in either of the following ways; each of the outside member and inside member is formed integrally; one of them is formed integrally while the other as an assembly of properly divided members of two parts or of four parts; the both members may be assemblies of divided members. The way of making the device can be determined according to the size and shape of the culture device.

Further, the material and structure of the sprinkled water receiver can be determined arbitrarily as long as the member can receive water streams sprinkled over and flowing down on the outside surface of the device. The material can be either a metal material or a plastic material.

The structure of the sprinkled water receiver can be either of the following; it is molded as a separate member from the culture device body; the receiver is constructed by extending the lower end of the outside member of the culture device horizontally around the outside periphery and bending the end portion upward; the sprinkled water receiver is constructed by extending the lower end of the inside member of the culture device horizontally around the outside periphery and bending the end portion upward.

A preferred configuration of the sprinkled water receiver is a member molded as a separate member from the culture device body.

The introducing member of air and/or carbonic acid gas provided in the bottom portion can be a tubular member having a lot of gas discharge ports, or gas discharge ports perforated in the bottom portion.

Since the gas introduced from this introducing member into the culture solution agitates the culture solution with moving up in the culture solution, the culture solution does not have to be mechanically agitated intentionally. This method can prevent the breakage of cells and the occurrence of shear stress due to the mechanical agitation accordingly.

The oxygen gas evolving in the photosynthesis can be discharged efficiently and quickly from the culture solution with the ascent of the gas.

There are two methods for supplying the culture solution into the culture device. The first method is a method for providing the bottom portion with a supply member (for example, a supply hole bored in the bottom portion) and supplying the culture solution through this supply member.

The second method is a method for supplying the culture solution through the cylindrical opening portion at the top part.

Provision of various supply and introducing members in the device will cause complication of the device and also have a problem of contamination on the occasion of change of the kind of microalgae to be cultured.

Therefore, the second method is most preferable.

Since the outside member and the inside member of the culture device both are made of the transparent material, if an artificial light source is provided in the inside space of the culture device the culture can also be carried out during the nighttime in the case of the outdoor culture. In the case of the indoor culture, efficient, continuous culture can be realized with two artificial light sources set inside and outside the culture device.

Since the culture device of the domed shape has a small occupying area but a large surface area, the light-receiving area thereof is large. In this device agitation of the culture solution is effected extremely well. When this device is made of a plastic material, it can be formed readily by vacuum forming and thus can be made at the lowest cost.

For these reasons, the culture device of the domed shape is most preferable as a microalgae culture device.

It is preferable to provide the culture device with various sensors such as a temperature sensor, a liquid level sensor, a pH sensor, a dissolved oxygen amount sensor, or the like for controlling and monitoring the culture conditions. These sensors are set through the cylindrical opening portion or through the outside wall of the device.

Since the gas discharge device of the present invention discharges the gas of air or the like obliquely downwardly toward the bottom portion of the culture device, it advances as hopping like a frog in the device. This motion causes the culture solution to be agitated hard and the discharged gas also agitates the culture solution during the ascent in the culture solution. Particularly, in cases where the microalgae to be cultured are likely to form colonies, the gas discharged from the gas discharge device breaks the colonies and disperses the microalgae in the culture solution, thereby increasing the culture efficiency.

The gas discharge device is normally made of a plastic material and is provided with the weight adjusting means to adjust the weight of the device.

The microalgae that can be cultured by the use of the culture device of the present invention include a variety of microalgae, in addition to Chlorella, Spirulina, and Dunaliella commercially successful heretofore. For example, such microalgae include those with excellent values added that produce useful substances, such as Haematococcus pluviaris producing β-ketocarotenoid (astaxanthin), Isochrysis galbana (Isocrysis galvana) being used as live bait for cultivation of marine fishes or producing a highly unsaturated fatty acid (DHA), Nannochloropsis oculata also being used as live bait for cultivation of marine fishes or producing a highly unsaturated fatty acid (EPA), and so on. The culture apparatus of the present invention can culture these microalgae in high concentrations and at high utilization efficiency of light.

BEST MODE FOR CARRYING OUT THE INVENTION

In order to explain the present invention in more detail, the culture devices and gas discharge devices according to the present invention will be described with reference to the accompanying drawings.

Figure 1:
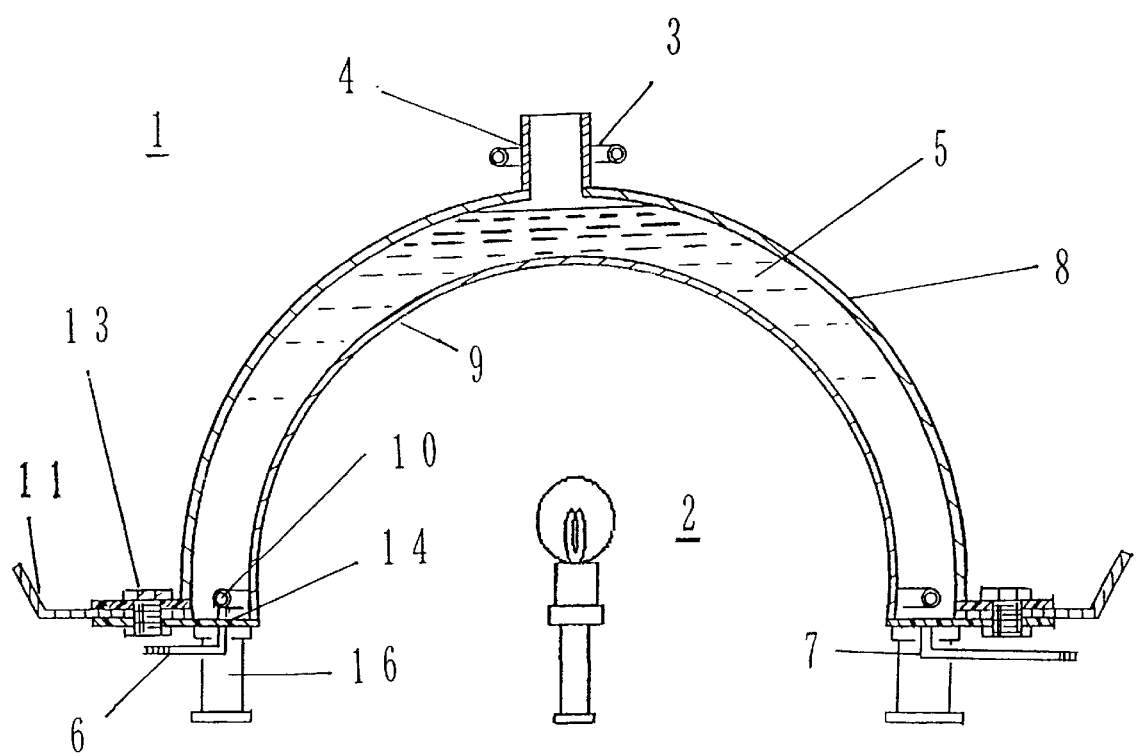
FIG. 1 is a sectional view of a culture device of the domed shape according to the present invention.
Figure 2:
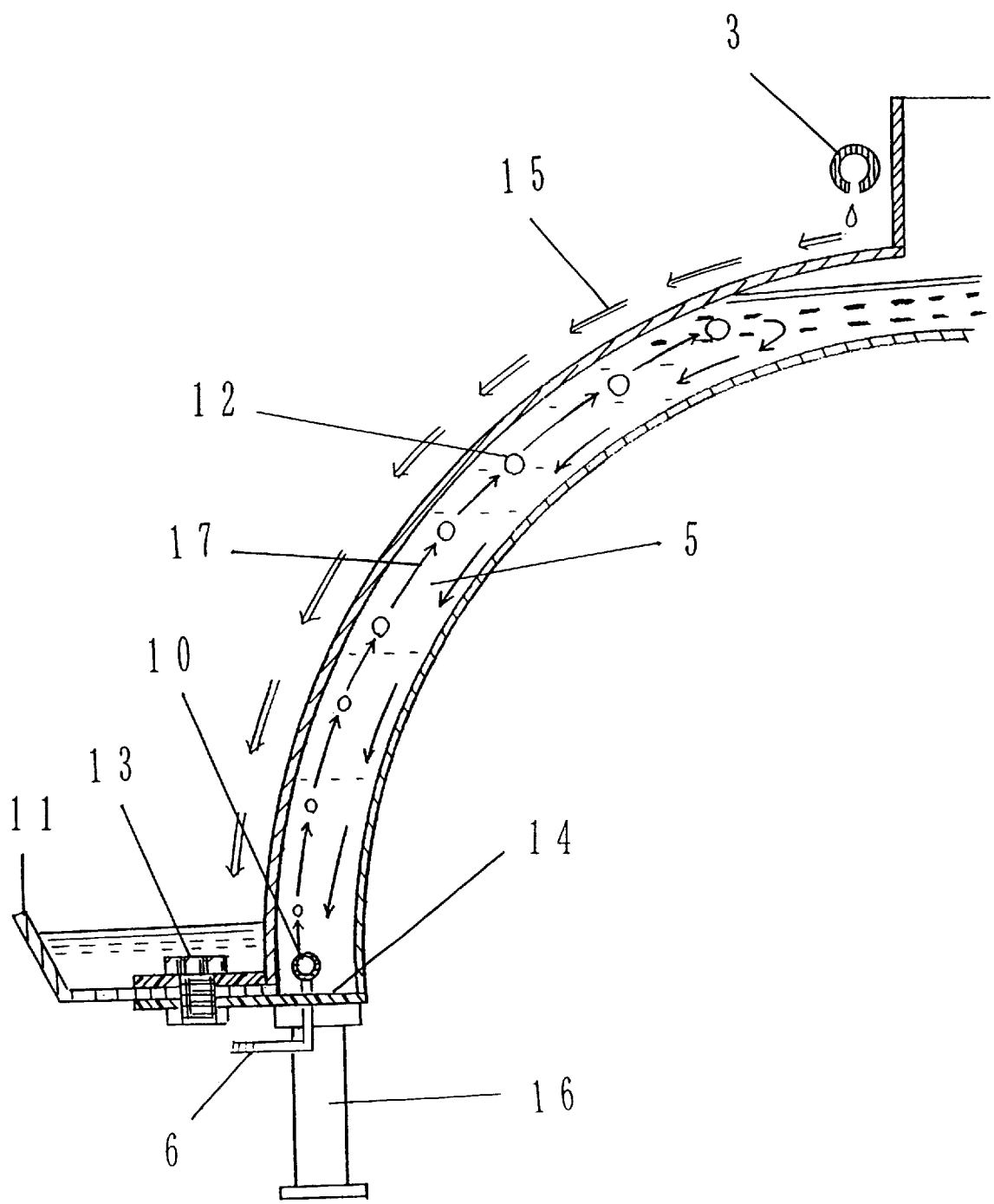
FIG. 2 is a partial, schematic view to show a state during the culture in the culture device of the domed shape illustrated in FIG. 1.
Figure 3:
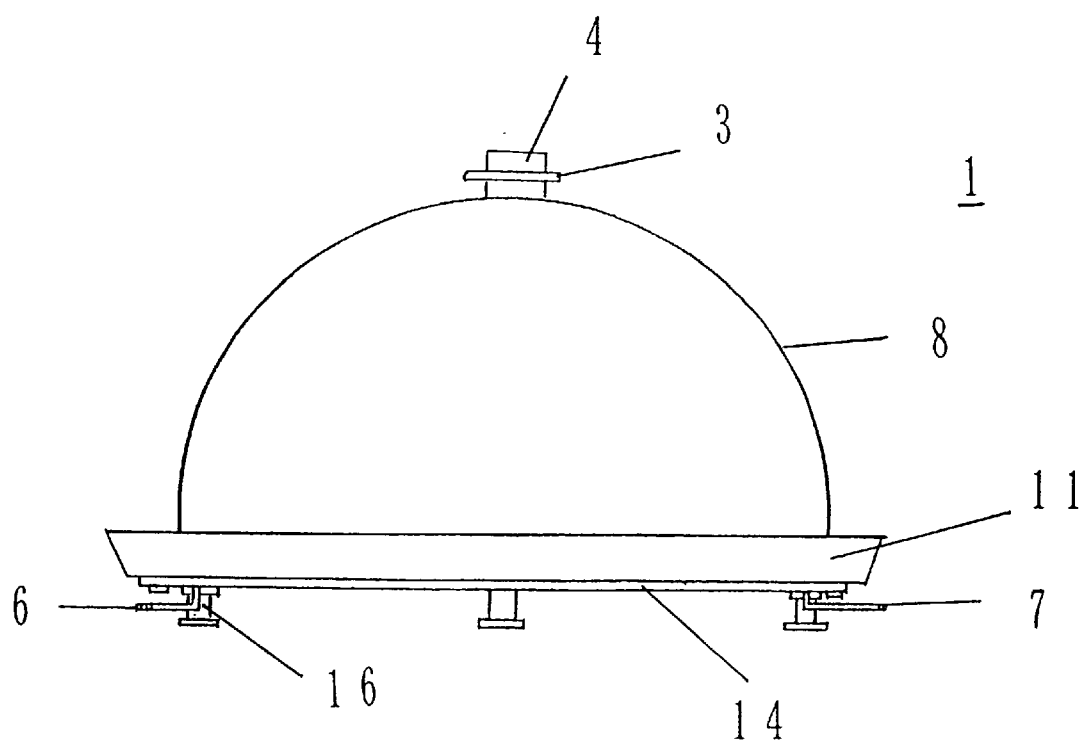
FIG. 3 is a front view of the culture device of the domed shape illustrated in FIG. 1.

FIG. 1 to FIG. 3 show the culture device 1 of the domed shape.

FIG. 3 is a front view of the culture device 1 of the domed shape, in which a cylindrical opening portion 4 is provided at the top part of outside semispherical dome 8, a water sprinkling member 3 for cooling the dome 8 is provided outside the cylindrical opening portion 4, a sprinkled water receiver 11 for receiving the water sprinkled from the sprinkling member 3 is provided at the lower part of the dome 8, and the device 1 is supported by a plurality of fixing members 16. A gas introducing member 6 and a discharging member 7 of the culture solution are attached to a bottom portion 14 of the culture device.

FIG. 1 is a sectional view of the device 1. This device 1 is constructed of the outside semispherical dome 8, an inside semispherical dome 9, and the bottom portion 14 for connecting the lower ends of the two domes. The cylindrical opening portion 4 is provided as a separate member at the top part of the dome 8, and the water sprinkling member 3 is provided outside the cylindrical opening portion 4, so that cooling water 15 is sprinkled from this water sprinkling member 3 over the surface of the dome 8 and drops with covering the surface of the dome 8 in the film form down to the sprinkled water receiver 11.

The temperature of the culture solution 5 is controlled by this cooling water 15 (see FIG. 2).

Each of the dome 8, dome 9, bottom portion 14, cylindrical opening portion 4, and sprinkled water receiver 11 is made of a transparent material. The transparent material used herein is the acrylic resin. A metallic material such as stainless steel or the like can also be preferably employed as a material for the sprinkled water receiver 11. The cooling water is drained off from the sprinkled water receiver 11 through a drain member (not illustrated). The water thus drained is stored and then is again used as cooling water.

Attached to the bottom portion 14 are the gas introducing member 6 for supplying air and/or carbonic acid gas into the culture solution 5 and the discharging member 7 for discharging the culture solution 5 from the culture device 1. A plurality of gas inlet pipes 10 having many inlet ports bored in an upper surface of pipe are disposed on the upper surface of the bottom portion 14, thus comprising part of the gas introducing member 6. The gas supplied from the gas introducing member 6 is most preferably air containing carbonic acid gas, but it may also be only air.

An artificial light source 2 is set in an inside space of the inside semispherical dome 9. The artificial light source 2 allows the microalgae to proceed with the photosynthesis even in the case of the outdoor culture during the nighttime. Further, in the case of the indoor culture, the photosynthesis can be advanced with artificial light sources set both outside and inside the culture device, and in this case the depth or thickness of the culture solution can be increased, if necessary.

FIG. 2 schematically shows a state during the culture. Bubbles 12 of the gas discharged from the gas inlet pipes 10 into the culture solution 5 move up in the culture solution 5 along the internal wall of the outside semispherical dome 8 because of their buoyancy. This upward motion of the bubbles 12 promotes upward motion of the culture solution, the carbonic acid gas included in the bubbles 12 is supplied into the culture solution, and the oxygen evolving in the photosynthesis of the microalgae is taken into the bubbles 12. The bubbles 12 are released into the atmosphere at the surface of the culture solution. A stream 17 of the culture solution moving up along the inner wall of the dome 8 descends along the wall of the inside semispherical dome 9.

As described above, the gas of air etc. supplied from near the bottom portion into the culture solution functions to supply the carbonic acid gas into the culture solution and take in the evolving oxygen gas to release it into the atmosphere on one hand and to uniformly agitate the culture solution on the other hand.

During the summer season, in which the culture can be hard because of a rise of the temperature of the culture solution, the cooling water 15 is supplied from the water sprinkling member 3 onto the surface of the outside semispherical dome 8, so as to control the temperature of the culture solution. The water used for the cooling is collected via the sprinkled water receiver 11 and is used again.

When in the outdoor culture the culture is also carried out during the nighttime, 24-hour continuous culture can be done by use of the artificial light source 2 disposed in the inside space of the inside semispherical dome 9.

The microalgae, receiving the sunlight during the daytime, actively carry out the photosynthesis to increase and also produce and store the useful substances such as the proteins, polysaccharides, fatty acids, pigments, vitamins, and so on, whereas in the nighttime, such photosynthesis is not carried out and the substances synthesized during the daytime are used because of energy consumption of the microalgae themselves; for example, in the summer season, the weight up to about 20% of the cells of algae is lost in the extreme case, when compared with that during the daytime, thus causing large loss.

In order to prevent this loss, the artificial light source is used to carry on the photosynthesis so as to compensate for the loss. Therefore, the artificial light source can be arranged to supply the quantity of light enough for minimum photosynthesis, but no trouble will be caused even if the photosynthesis more than that is carried out. The artificial light source can be one selected, for example, from a fluorescent tube, an incandescent lamp, a halogen lamp, and so on.

In the case of the indoor culture the artificial light sources can be used both outside and inside the culture device 1. The use of the artificial light sources 2 in this way permits efficient, continuous culture for 24 hours.

For monitoring the culture conditions, it is necessary to always measure the temperature, the liquid level, pH, and dissolved oxygen amount (DO) of the culture solution and keep each of numerical values of these factors within an optimum range. It is thus desirable to attach sensors of these factors to the device, and they are preferably set through the cylindrical opening portion 4 at the top part or through either the dome 8 or the dome 9 or through the both. If they are attached to the dome the device will become complicated and considerable labor and time will be necessary for cleaning etc.; therefore, they are most preferably set through the cylindrical opening portion 4.

This culture device 1 of the domed shape can be constructed of an arbitrary combination of two types of semispherical domes having respective radii different from each other, and this structure permits change in the volume of the space formed between the two domes and change in the distance between the domes. This means that the amount of the culture solution and the thickness or depth of the culture solution can be set freely.

Further, the microalgae attach to the surfaces of the device in contact with the culture solution and thus, for the removal and cleaning of this attachment, the outside semispherical dome 8, out of the two types of the semispherical domes combined, is detached, so as to permit each of the domes to be cleaned; or the both domes can also be detached to be cleaned at different locations.

For the semispherical domes, it is very convenient to employ an assembly, for example, of two components as the outside semispherical dome. In either case, each of the two types of domes does not have to be an integrally molded member, but can be an assembly of plural molded components.

The shape of the semispherical domes can be any semisphere-like dome shape obtained by cutting a sphere at an arbitrary position, but the most preferable shape is approximately semispherical in terms of the utilization efficiency of light and reception of light.

The present invention also embraces modified spherical shapes including an egg shape etc., in addition to the spherical shapes.

The size of the domes applicable is, for example, about 50 cm to about 200 cm in diameter, and the culture device can be constructed by arbitrarily selecting a proper size according to the kind of microalgae to be cultured, the culture conditions, and the culture purpose.

The spacing between the two types of domes can be set so as to obtain the maximum photosynthesis efficiency, though depending upon the kind of microalgae, the culture conditions, and the culture purpose. Normally, the spacing is preferably 2.5 cm to 10 cm and more preferably about 5 cm.

The domed culture device 1 having the dome spacing of 5 cm was constructed of the outside semispherical dome 8 having the radius of about 50 cm and the inside semispherical dome having the radius of about 45 cm, and the cylindrical opening portion 4 molded as a separate member from the domes and having the diameter of 6 cm was provided at the top part of the dome 8.

The microalgae, Spirulina Platencis, were cultured by the use of this culture device, whereby the culture concentration of 10 to 20 g/liter and the productivity of 2.0 to 5.0 g/liter/day were realized. On the other hand, in the case of the conventional culture pond method, the culture concentration is 0.3 to 0.5 g/liter and the productivity is 0.1 to 0.2 g/liter/day. It was thus verified that the productivity was enhanced to about ten times that of the conventional culture method.

It was also verified in the culture of Haematococcus Pluviaris producing astaxanthin of a red pigment that it was possible to produce algal bodies (biomasses) containing a high content of 4% to 8% of the pigment, astaxanthin, by high concentration culture in the culture concentration of 5 g to 10 g/liter. The culture of Haematococcus Pluviaris producing this red pigment was very difficult in the conventional culture pond method. Moreover, the high concentration culture of about 5 g to 10 g/liter was also able to be carried out with the marine algae of Nannochloropsis Oculata. The maximum concentration by the conventional method was 0.2 to 0.4 g/liter.

Figure 4:
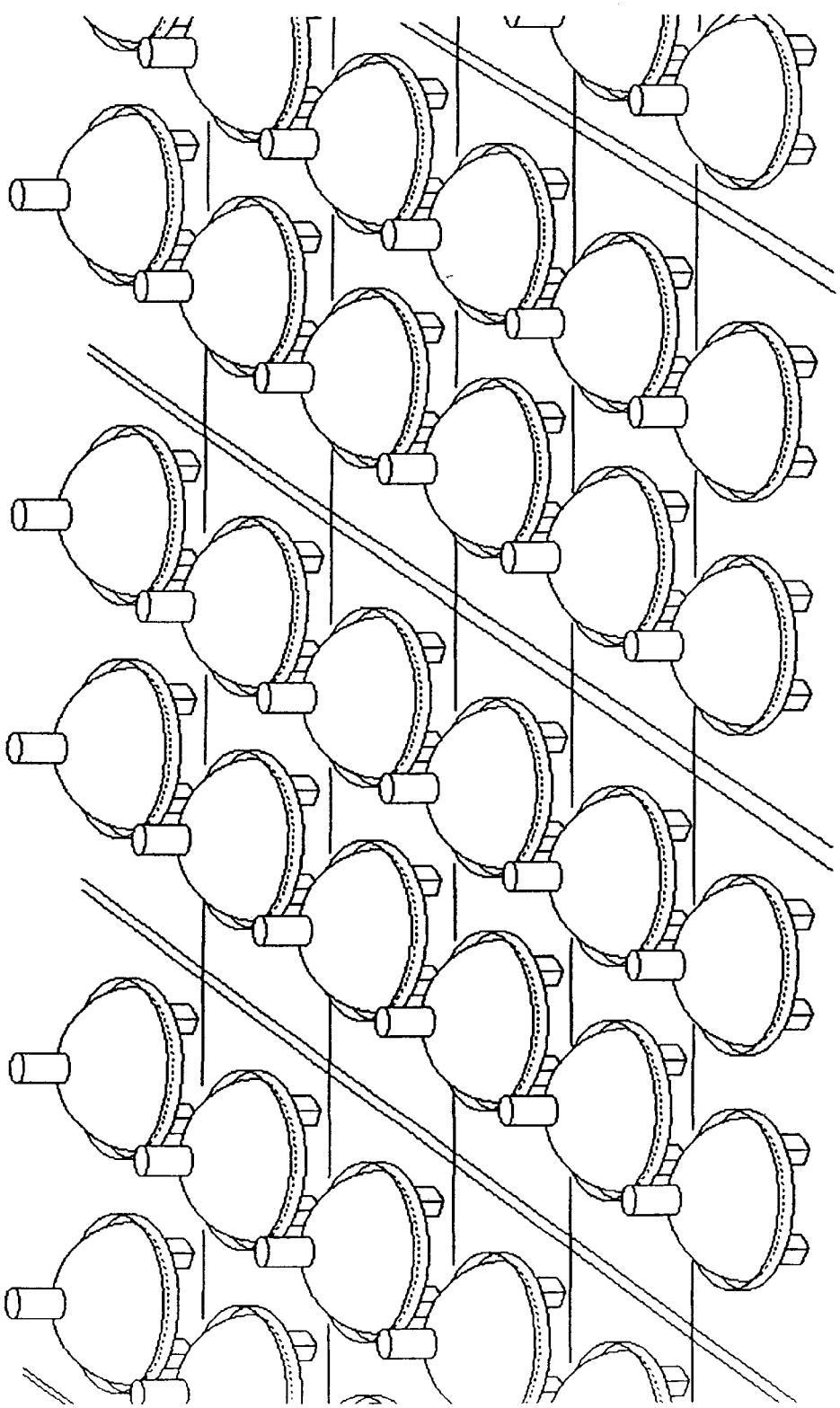
FIG. 4 is an explanatory diagram to show a mass culture system of microalgae utilizing the culture devices of the domed shape illustrated in FIG. 1 to FIG. 3.

FIG. 4 shows a system in which a lot of closed outdoor culture devices according to the present invention are placed and which can culture the microalgae simultaneously and in volume. In the system, the microalgae of the same kind may be put and cultured simultaneously in the individual component devices or the microalgae of different kinds may be put and cultured separately in the individual devices. Each of the devices is equipped with the various sensors so as to be able to control the culture conditions.

This structure is very effective because the various culture conditions of the individual devices can be controlled independently even if the microalgae of different kinds are cultured in the individual devices.

Further, even if the devices are arranged in rather dense relation, the utilization efficiency of light or the light-receiving area of light per occupying area is large; thus the structure is very convenient and suitable for volume culture and the productivity is very high.

Figure 5:
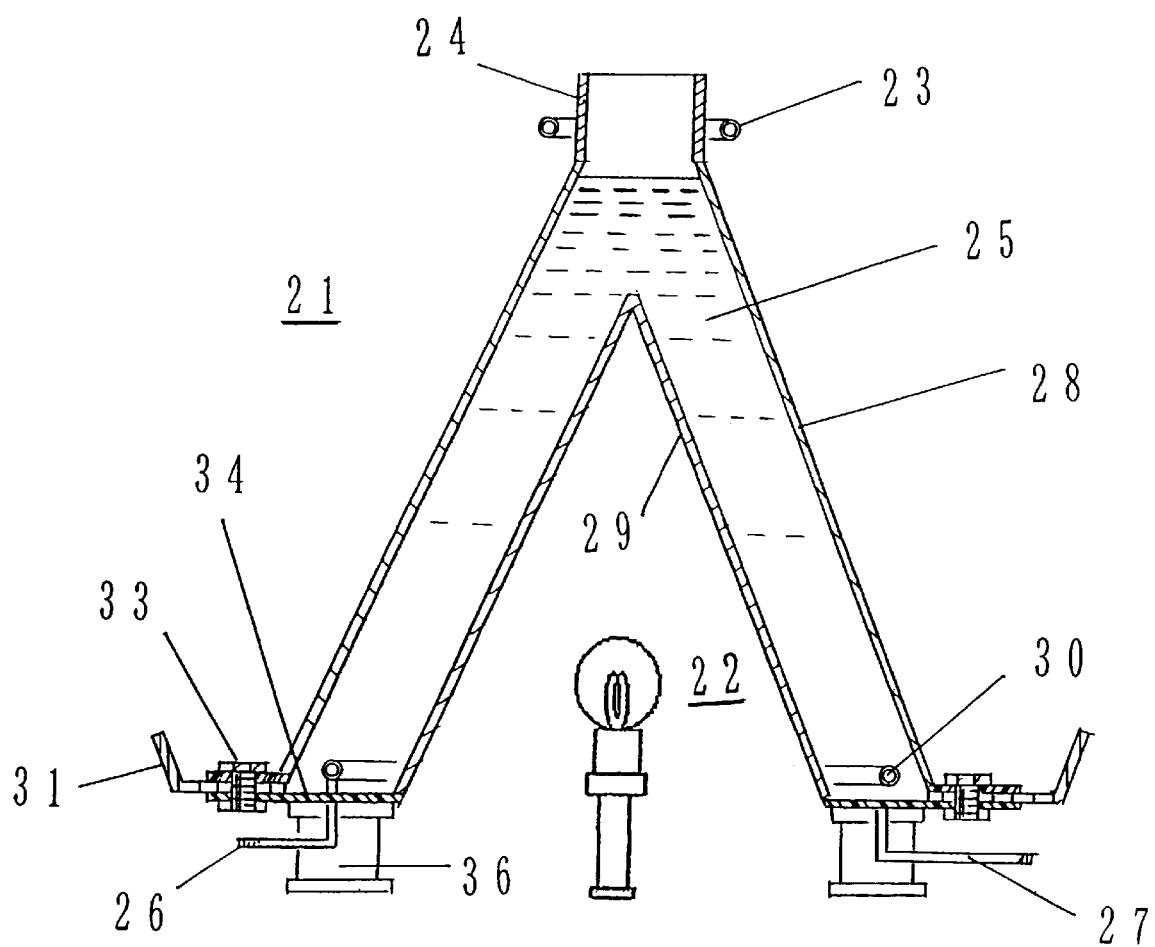
FIG. 5 is a sectional view of a culture device of the conical shape according to the present invention.
Figure 6:
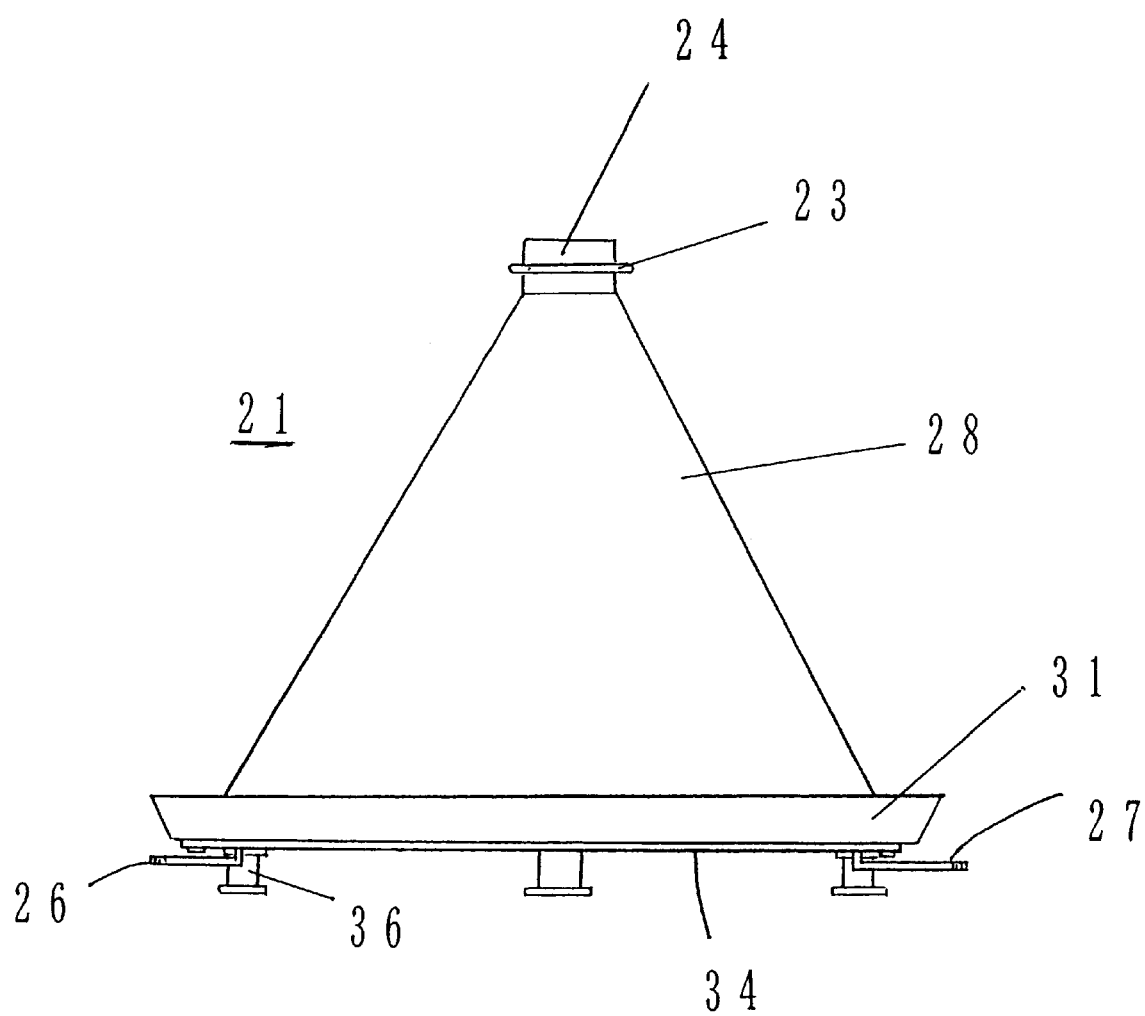
FIG. 6 is a front view of the culture device of the conical shape of FIG. 5.

FIG. 5 and FIG. 6 show the culture device 21 of the conical shape.

FIG. 6 is a front view of the culture device 21 of the conical shape, in which the cylindrical opening portion 24 is provided at the top part of outside conical peripheral wall 28 made of the transparent material, the sprinkled water member 23 for cooling the peripheral wall 28 is provided outside this opening portion 24, the sprinkled water receiver 31 for receiving the cooling water sprinkled from the water sprinkling member 23 is provided at the lower part of the peripheral wall 28, and the device 21 is supported by a plurality of fixing members 36.

Further, the gas introducing member 26 and the discharging member 27 of the culture solution are attached to the bottom portion 34 of the device 21.

FIG. 5 is a sectional view of the device 21. This device 21 is comprised of the outside conical peripheral wall 28 of the transparent material, an inside conical peripheral wall 29 of the transparent material, and the bottom portion 34 for connecting the lower ends of the two peripheral walls. The cylindrical opening portion 24 is provided as a separate member at the top part of the outside conical peripheral wall 28 and the water sprinkling member 23 is provided outside the opening portion 24 so that the cooling water is sprinkled from this water sprinkling member 23 over the surface of the peripheral wall 28 to drop with covering the surface of the peripheral wall 28 in the film form down into the sprinkled water receiver 31. The temperature of the culture solution 25 is controlled by the cooling water.

Each of the peripheral wall 28, peripheral wall 29, bottom portion 34, cylindrical opening portion 24, and sprinkled water receiver 31 is made of the transparent material such as the acrylic resin.

The cooling water from the sprinkled water receiver 31 is drained off through the drain member (not illustrated).

Attached to the bottom portion 34 are the gas introducing member 26 for supplying air and/or carbonic acid gas into the culture solution 25 and the discharging member 27 for discharging the culture solution 25 from the device 21. A plurality of gas inlet pipes 30 having a lot of gas inlet ports bored in the upper surface of pipe are provided on the upper surface of the bottom portion 34, thus comprising part of the gas introducing member 26. Further, the artificial light source 22 is provided in the inside space of the peripheral wall 29, so that the photosynthesis can be carried out continuously during the nighttime in the outdoor culture.

Figure 7:
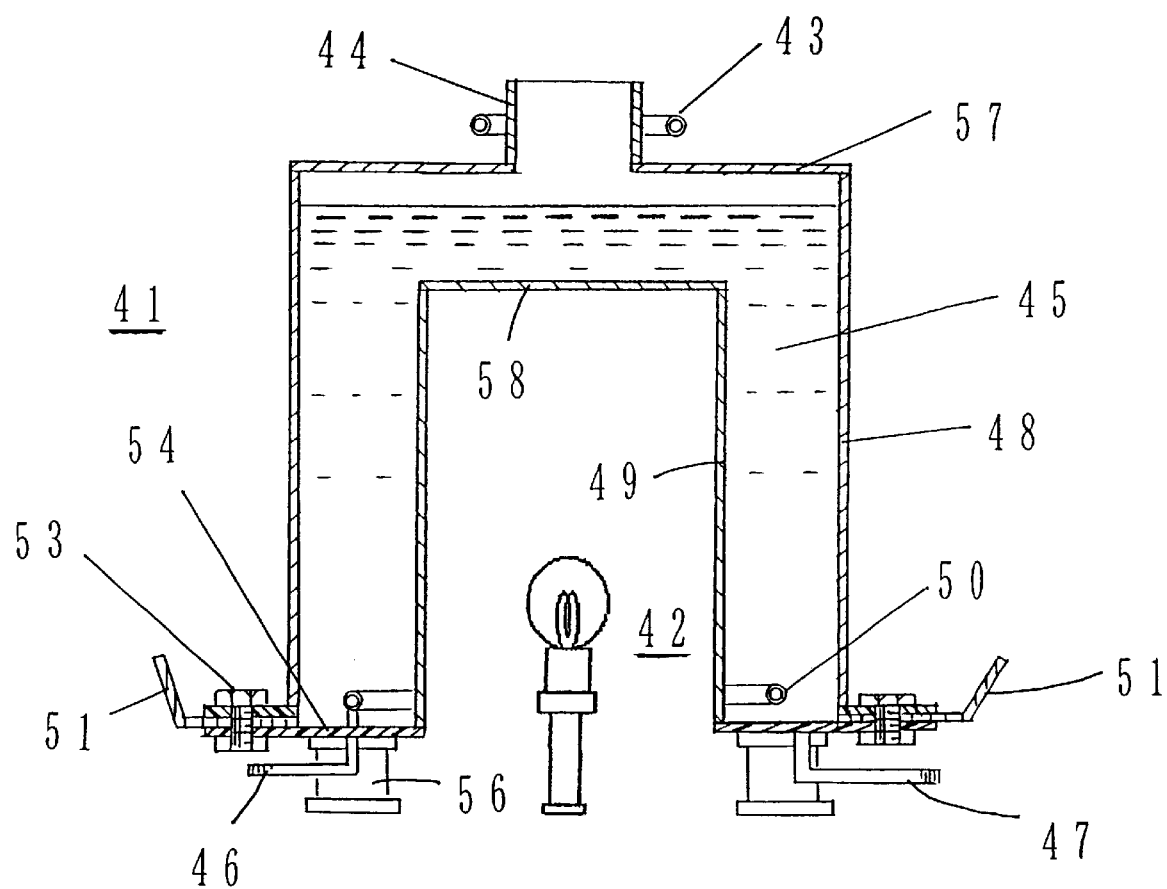
FIG. 7 is a sectional view of a culture device of the cylindrical shape according to the present invention.
Figure 8:
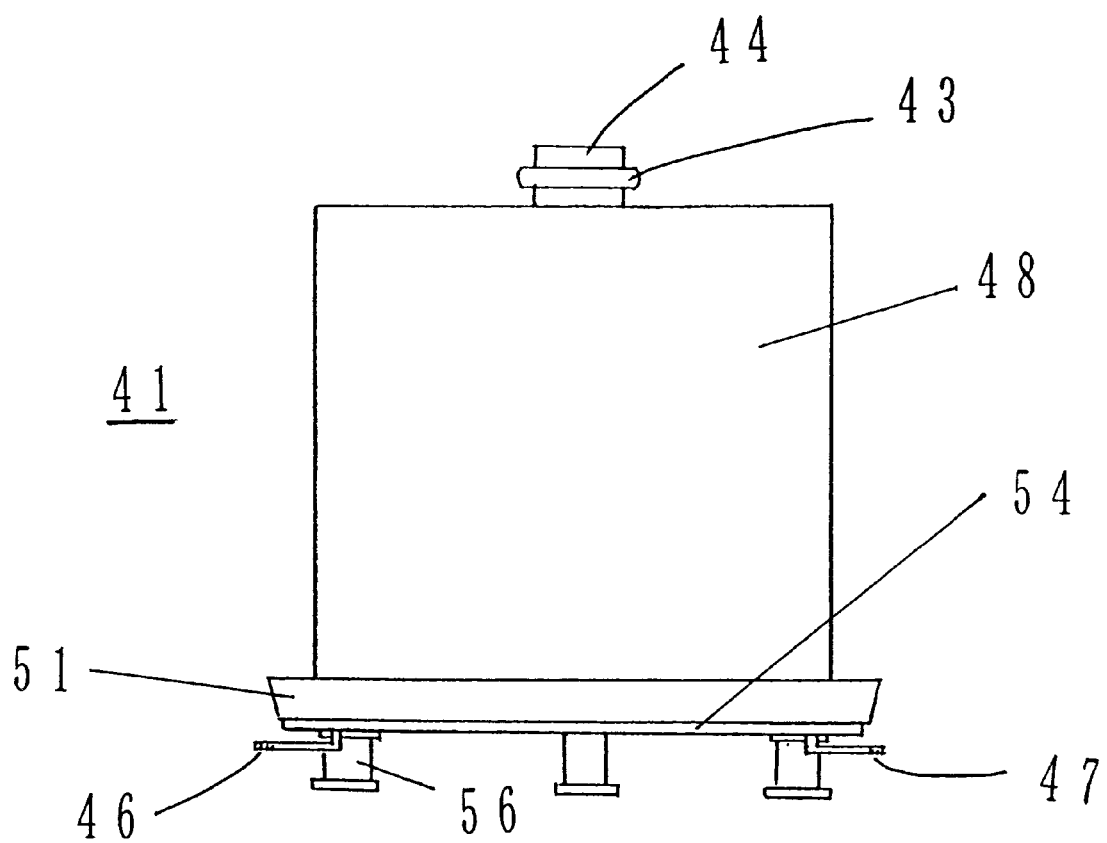
FIG. 8 is a front view of the culture device of the cylindrical shape of FIG. 7.

FIG. 7 and FIG. 8 show the culture device 41 of the cylindrical shape.

FIG. 8 is a front view of the culture device 41 of the cylindrical shape, in which the cylindrical opening portion 44 is provided near the central part of an upper wall of outside cylindrical peripheral wall 48 made of the transparent material and having the upper wall 57, the water sprinkling member 43 for cooling the upper wall 57 and peripheral wall 48 is provided outside this opening portion 44, the sprinkled water receiver 51 for receiving the cooling water sprinkled from the water sprinkling member 43 is provided at the lower part of the peripheral wall 48, and the device 41 is supported by a plurality of fixing members 56.

Further, the gas introducing member 46 and the discharging member 47 of the culture solution are attached to the bottom portion 54 of the device 41.

FIG. 7 is a sectional view of the device 41. The device 41 is composed of the outside cylindrical peripheral wall 48 having the upper wall 57, an inside cylindrical peripheral wall 49 having an upper wall 58, and the bottom portion 54 for connecting the lower ends of the two peripheral walls. The cylindrical opening portion 44 is integrally formed near the central part of the upper wall 57, and the water sprinkling member 43 is provided outside the opening portion 44 so that the cooling water is sprinkled from this sprinkling member 43 over the upper wall 57 to drop with covering the surface of the peripheral wall 48 in the film form down to the sprinkled water receiver 51.

The temperature of the culture solution 45 can be controlled by the cooling water.

Each of the peripheral wall 48, peripheral wall 49, upper wall 57, upper wall 58, cylindrical opening portion 44, and sprinkled water receiver 51 is made of the transparent material such as the acrylic resin.

The cooling water is drained off from the sprinkled water receiver 51 through the drain member (not illustrated). Attached to the bottom portion 54 are the gas introducing member 46 for supplying the gas into the culture solution and the discharging member 47 for discharging the culture solution 45 from the device 41. A plurality of gas inlet pipes 50 having many gas inlet ports bored in the upper surface of pipe are provided on the upper surface of the bottom portion 54, thus comprising part of the gas introducing member 46.

Further, the artificial light source 42 is provided in the inside space formed by the upper wall 58 and the peripheral wall 49, so as to permit the photosynthesis during the nighttime.

Figure 13:
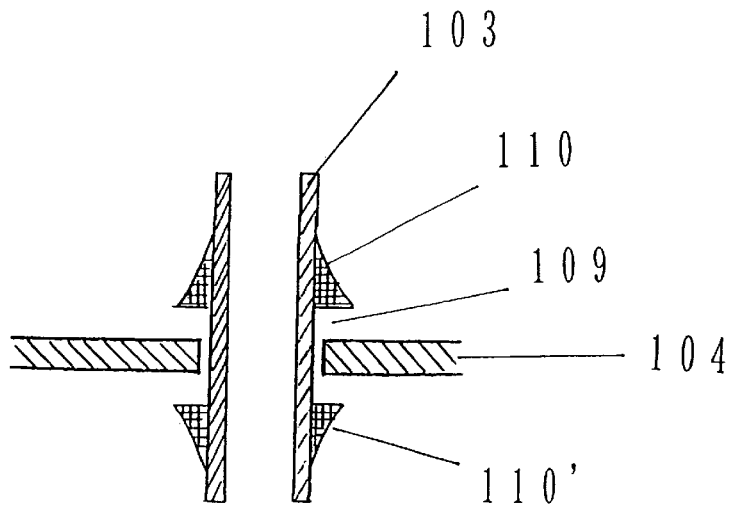
FIG. 13 is an enlarged sectional view of a discharge nozzle of the gas discharge device of FIG. 9.

FIG. 9 to FIG. 12 are a perspective view, a side view, a plan view, and a sectional view, respectively, of the gas discharge device 100, and FIG. 13 is an enlarged sectional view of a discharge nozzle of the gas discharge device.

The gas discharge device 100 is comprised of rectangular base plates 101, 101' opposed to each other, a bubble guide member 102 of a ⊓-shaped cross section opening down, and a discharge nozzle 103, the bubble guide member 102 being inclined with respect to upper surfaces 107, 107' of the rectangular base plates and having an inclined wall 104 as an upper surface and an upper wall 105 almost horizontally extending at the upper end thereof, the bubble guide member 102 also having side walls 106, 106' hanging down from the both side edges of the inclined wall 104 and upper wall 105, the lower ends of the two side walls 106, 106' being joined to the upper surfaces 107, 107' of the two rectangular base plates 101, 101'. The both rectangular base plates are fixed to each other by fixing members 108, 108'.

The discharge nozzle 103 is provided through a through hole 109 bored in the lower part of the inclined wall 104 so as to be rotatable. Stoppers 110, 110' are located at opposed positions on either side of the through hole 109 on the outer periphery of the nozzle 103 so as to prevent the nozzle 103 from slipping off the through hole 109.

Figure 11:
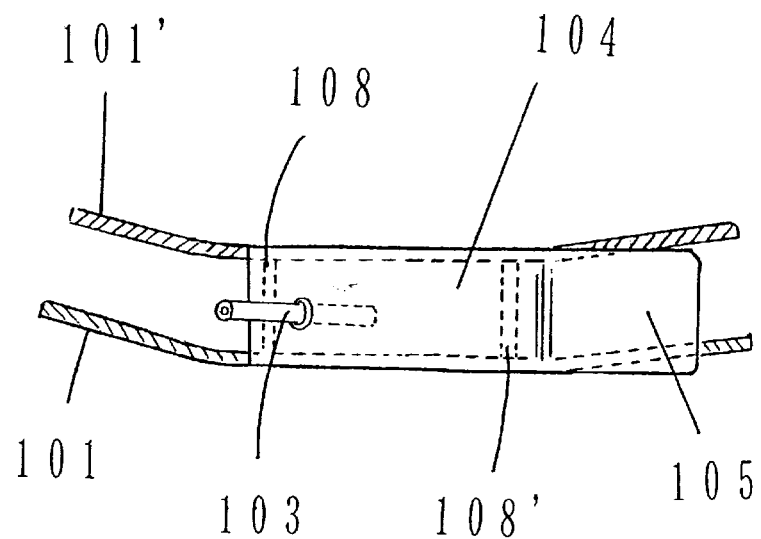
FIG. 11 is a plan view of the gas discharge device of FIG. 9.
Figure 12:
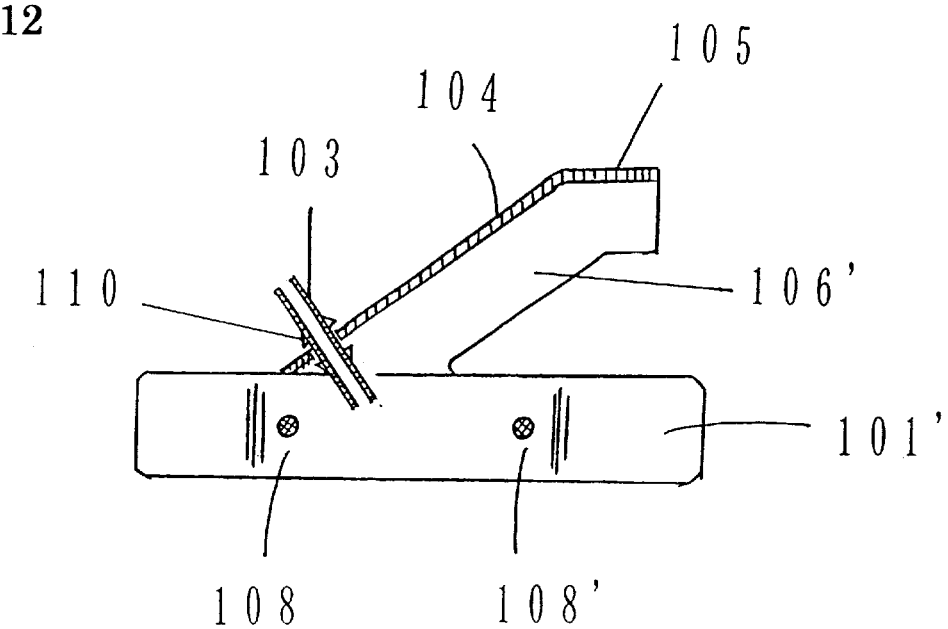
FIG. 12 is a sectional view of the gas discharge device of FIG. 9.

In either type of the main body of the culture device, i.e., in either of the domed shape, the conical shape, and the cylindrical shape, the inside edge and outside edge of the bottom portion are the circumferences of concentric circles and the bottom portion is thus of a circular shape obtained by cutting a central portion out of a disk. In order to permit easy movement on the bottom portion of the bored circle shape, the front and rear portions of the rectangular base plates 101, 101' are bent in the same direction as illustrated in FIG. 11.

An angle of inclination of the inclined wall 104 is preferably designed so as to be 45° to 60° with respect to the upper surfaces of the rectangular base plates.

Figure 14:
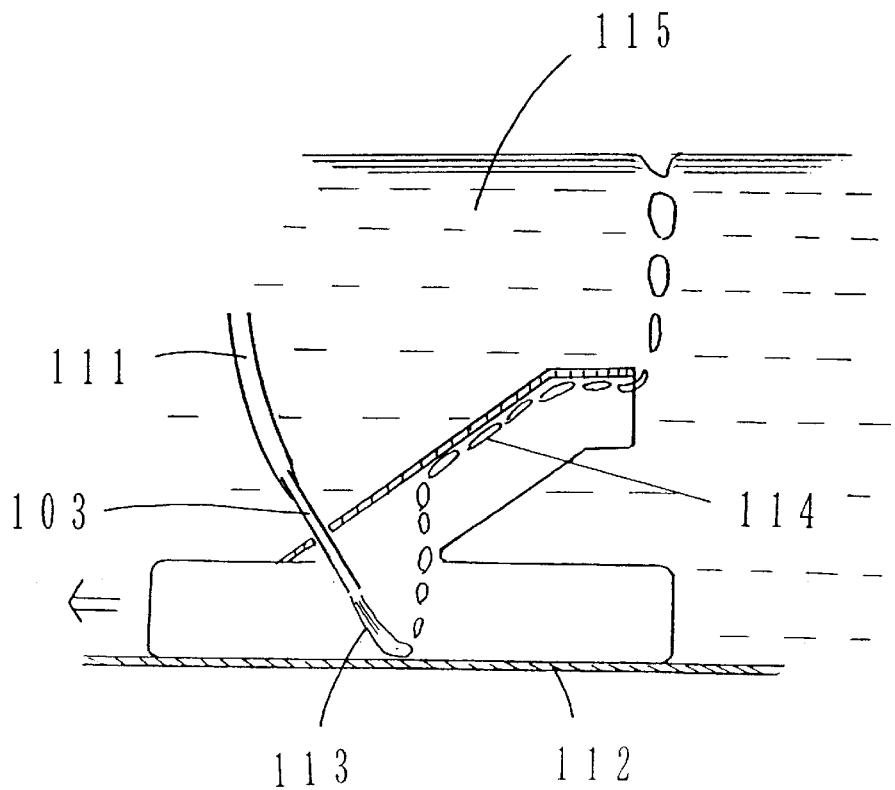
FIG. 14 is a sectional, explanatory drawing to show a state in which the gas discharge device is discharging the gas into the culture solution.

FIG. 14 is an explanatory drawing to show a state in which the gas discharge device is discharging the gas into the culture solution.

The gas of air or air containing carbonic acid gas is supplied from a gas supply device (not illustrated) provided separately from the culture device, through a gas inlet tube 111 to the discharge nozzle 103 and is then discharged from the tip portion of the nozzle toward the bottom portion 112 of the culture device. The gas 113 discharged hits the bottom portion 112 and thereafter moves up in the form of bubbles 114 inside the bubble guide member 102, i.e., along the inclined wall 104 and upper wall 105 to be fed from the end of the upper wall 105 into the culture solution 115. The bubbles 114 thus fed move up in the solution to be discharged to the atmosphere at the surface of the culture solution. While the gas is in contact with the culture solution, the culture solution absorbs the carbonic acid gas, whereas the gas takes in the oxygen evolving in the photosynthesis of algae and forming bubbles or being dissolved in the culture solution. The bubbles 114 also push up the solution during the upward motion in the culture solution, thereby causing convection of the solution.

The gas and bubbles 114 discharged from the tip end of the discharge nozzle 103 bring about the buoyancy of the gas discharge device itself and a thrust in the direction indicated by an arrow. This causes the gas discharge device 100 to move in a floating state in the direction of the arrow. The device repeatedly performs such operation as to land on the bottom portion because of the weight of the device 100 after some movement and then float to move ahead; this operation makes the culture solution agitated heavily. This operation of the gas discharge device in the culture solution is similar to the motion of a frog hopping ahead.

The members forming the gas discharge device 100 are normally made of plastics, but many plastics themselves are considerably lightweight, in addition to the buoyancy in the culture solution; therefore, they are either those molded of a material obtained by adding a filler with a large specific weight into a plastic material to add some weight, artificial-stone-like members formed in lamination by bonding stone powder or filler powder to the rectangular base plates 101, 101' with synthetic resin such as the epoxy resin or the like, those obtained by forming the lower part of the rectangular base plates 101, 101' of an artificial-stone-like material and forming the upper part of a plastic material, or those permitting adjustment of the total weight of the gas discharge device 100 by detachable arrangement of weights of metal such as lead or the like at arbitrary positions on opposed surfaces of the rectangular base plates 101, 101'; among them, the most preferable members are those permitting the adjustment of the total weight.

Figure 15:
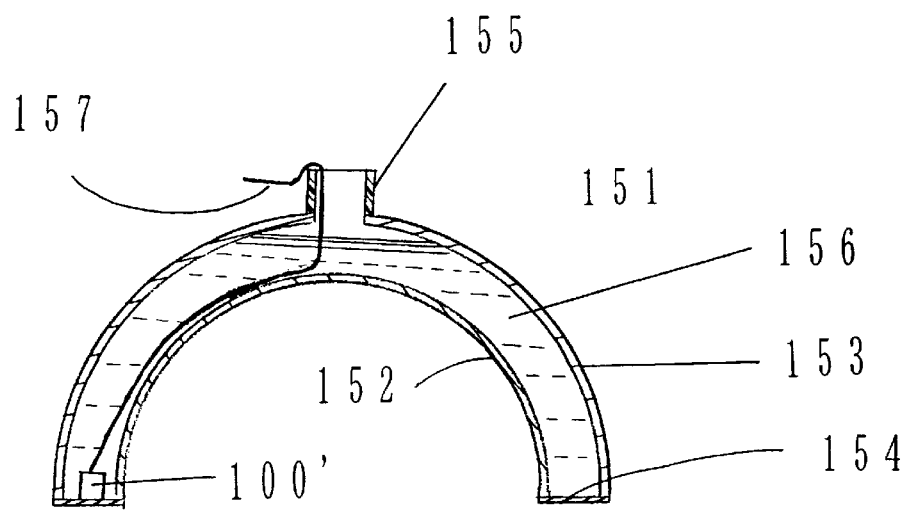
FIG. 15 is a sectional, explanatory drawing of a culture apparatus as a combination of the culture device of the domed shape itself with the gas discharge device.
Figure 16:
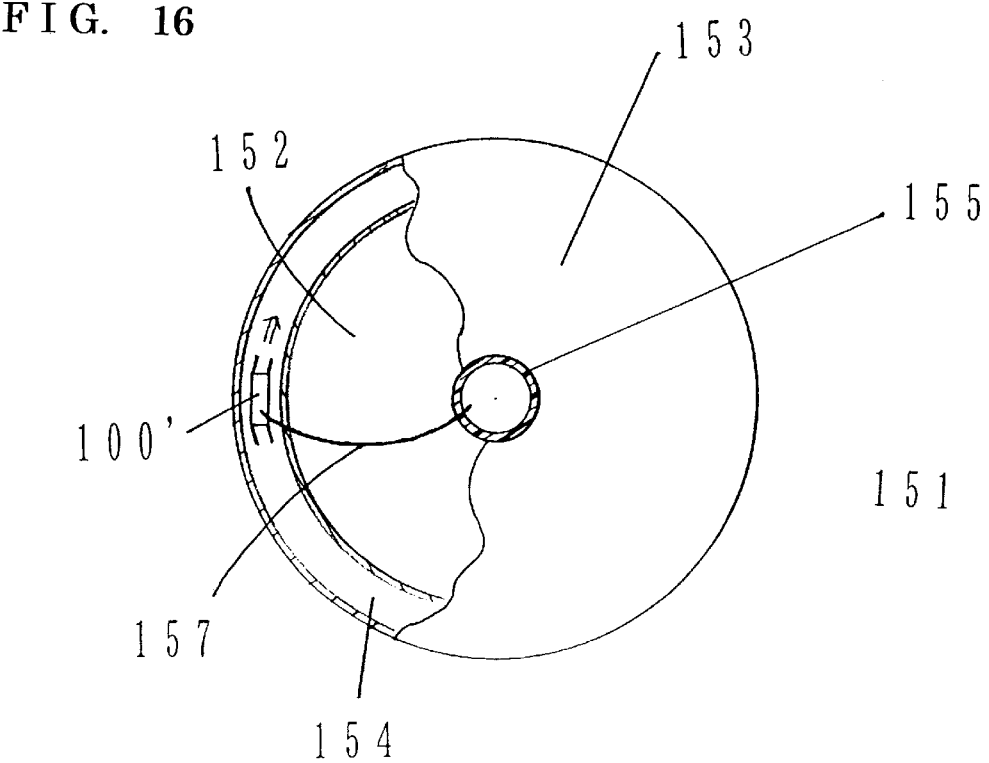
FIG. 16 is a top plan view, partly broken, of FIG. 15.

FIG. 15 is a sectional, explanatory view of a culture apparatus 150 as a combination of the culture device body 151 of the domed shape with the gas discharge device 100' and FIG. 16 is a top plan view thereof, partly broken.

Here, the culture device body 151 is comprised of an outside semispherical dome 153, an inside semispherical dome 152, and a bottom portion 154 for connecting the lower ends of the two domes, a cylindrical opening portion 155 is provided at the top part of the dome 153, and the description of the other members is omitted herein.

All of these members are made of the transparent material, which is, for example, the acrylic resin.

The gas discharge device 100' to which the gas inlet tube 157 is connected is put through the cylindrical opening portion 155 of the culture device body 151 and placed on the bottom portion 154.

The gas inlet tube 157 is made of a material selected from polyurethane, silicone, synthetic rubber, and so on, and is in contact with the surface of the inside semispherical dome 152.

While the gas of air or the like is supplied to the gas discharge device 100', this device 100' advances in the moving direction of an arrow with hopping in the culture solution. On this occasion the culture solution is agitated sufficiently by the discharged gas and the motion of the gas discharge device.

Since the gas discharge device 100' moves ahead on the bottom portion 154 of the annular shape, the device 100' circularly moves on the bottom portion 154 while the gas inlet tube 157 connected thereto rubs or cleans the surface of the inside semispherical dome 152, as illustrated in FIG. 16. Namely, the device 100' performs the circular motion on the bottom portion 154 with the gas inlet tube 157 rubbing or cleaning the surface of the dome 152. This means that the gas inlet tube 157 acts to prevent the algae from attaching to the surface and also clean the surface.

Since the gas discharge device 100' moves while agitating the culture solution 156, the algae likely to form colonies, if present, will be broken and again dispersed in the culture solution, so that the culture can be carried out very efficiently.

On this occasion, the gas inlet tube is twisted, but the discharge nozzle is free to rotate as illustrated in FIG. 13; therefore, the discharge nozzle rotates in the through hole to cancel the twist.

Figure 17:
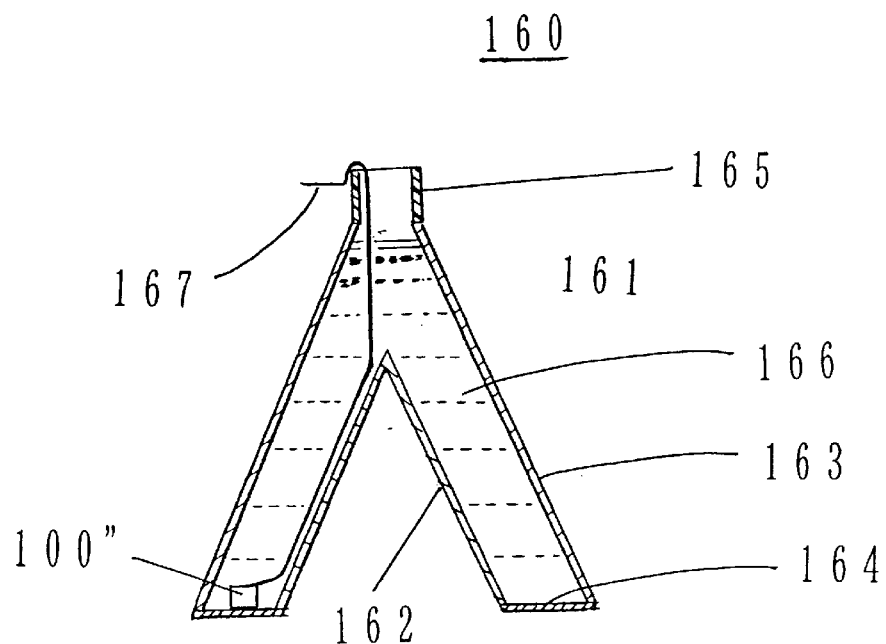
FIG. 17 is a sectional, explanatory drawing of a culture apparatus as a combination of the culture device of the conical shape itself with the gas discharge device.

FIG. 17 is a sectional, explanatory view of a culture apparatus 160 as a combination of the gas discharge device 100" with the culture device body 161 of the conical shape.

Here, the culture device body 161 is comprised of an outside conical peripheral wall 163 of the transparent material, an inside conical spherical wall 162 of the transparent material, and a bottom portion 164 for connecting the lower ends of the two peripheral walls, and a cylindrical opening portion 165 of the transparent material is provided at the top part of the peripheral wall 163. The description of the other members is omitted herein.

The gas discharge device 100" to which the gas inlet tube 167 is connected is put through the cylindrical opening portion 165 and is placed on the bottom portion 164.

While the gas of air or the like is supplied to the gas discharge device 100", this device 100" repeats the forward motion while hopping in the culture solution. This motion is just as described with the culture apparatus of FIG. 15 and FIG. 16.

Figure 18:
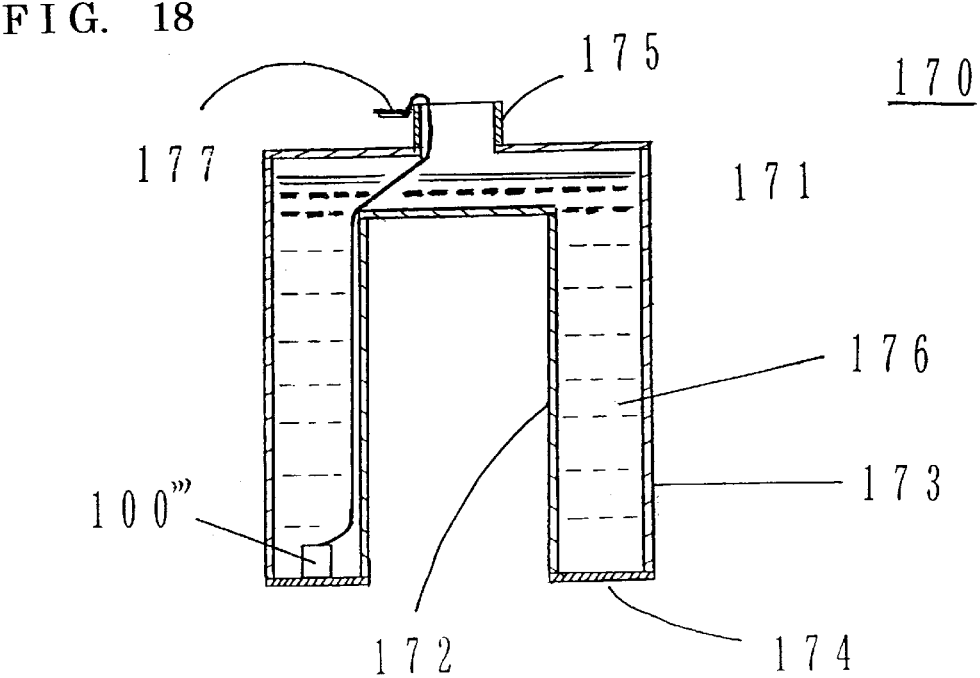
FIG. 18 is a sectional, explanatory drawing of a culture apparatus as a combination of the culture device of the cylindrical shape itself with the gas discharge device.

FIG. 18 is a sectional, explanatory view of a culture apparatus 170 as a combination of the gas discharge device 100''' with the culture device body 171 of the cylindrical shape.

Here, the culture device body 171 is comprised of an outside cylindrical peripheral wall 173 having an upper wall of the transparent material, an inside cylindrical peripheral wall 172 having an upper wall of the transparent material, and a bottom portion 174 for connecting the lower ends of the two peripheral walls, and a cylindrical opening portion 175 of the transparent material is provided in the central part of the upper wall of the outside cylindrical peripheral wall 173. The description of the other members is omitted herein.

The gas discharge device 100''' to which the gas inlet tube 177 is connected is put through the cylindrical opening portion 175 and is placed on the bottom portion 174.

While the gas of air or the like is supplied to the gas discharge device 100''', this device 100''' repeats the forward motion while hopping in the culture solution. This motion is just as described with the culture apparatus of FIG. 15 and FIG. 16.

Figure 19:
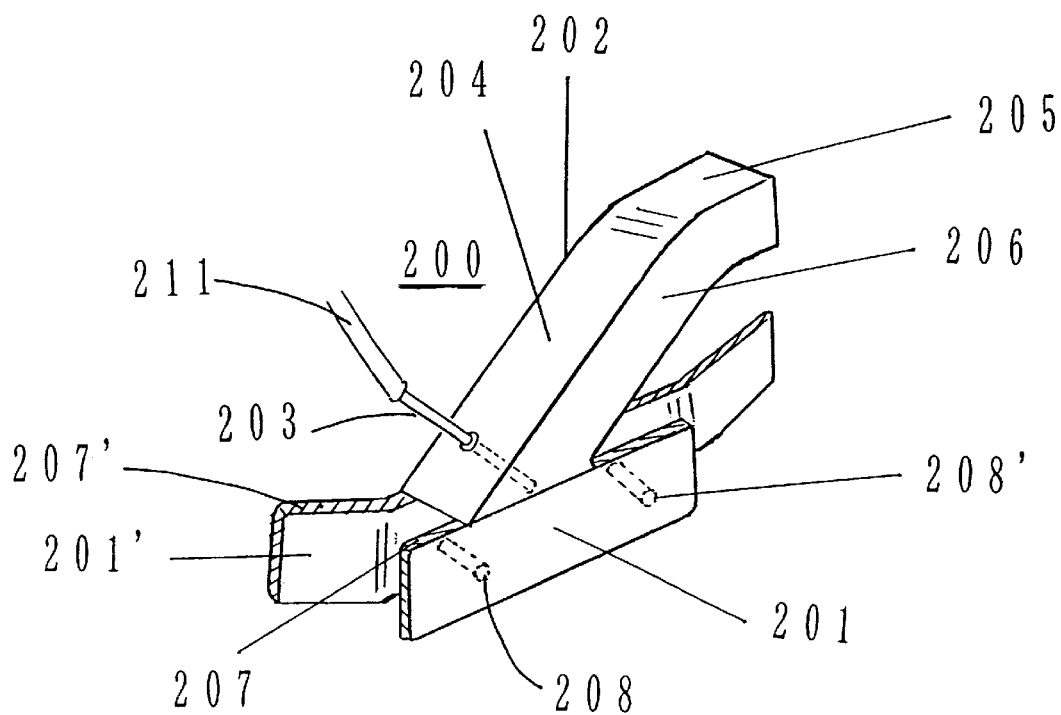
FIG. 19 is a perspective view to show another example of the gas discharge device of the present invention.

FIG. 19 is a perspective view to show another embodiment of the gas discharge device of the present invention.

Figure 9:
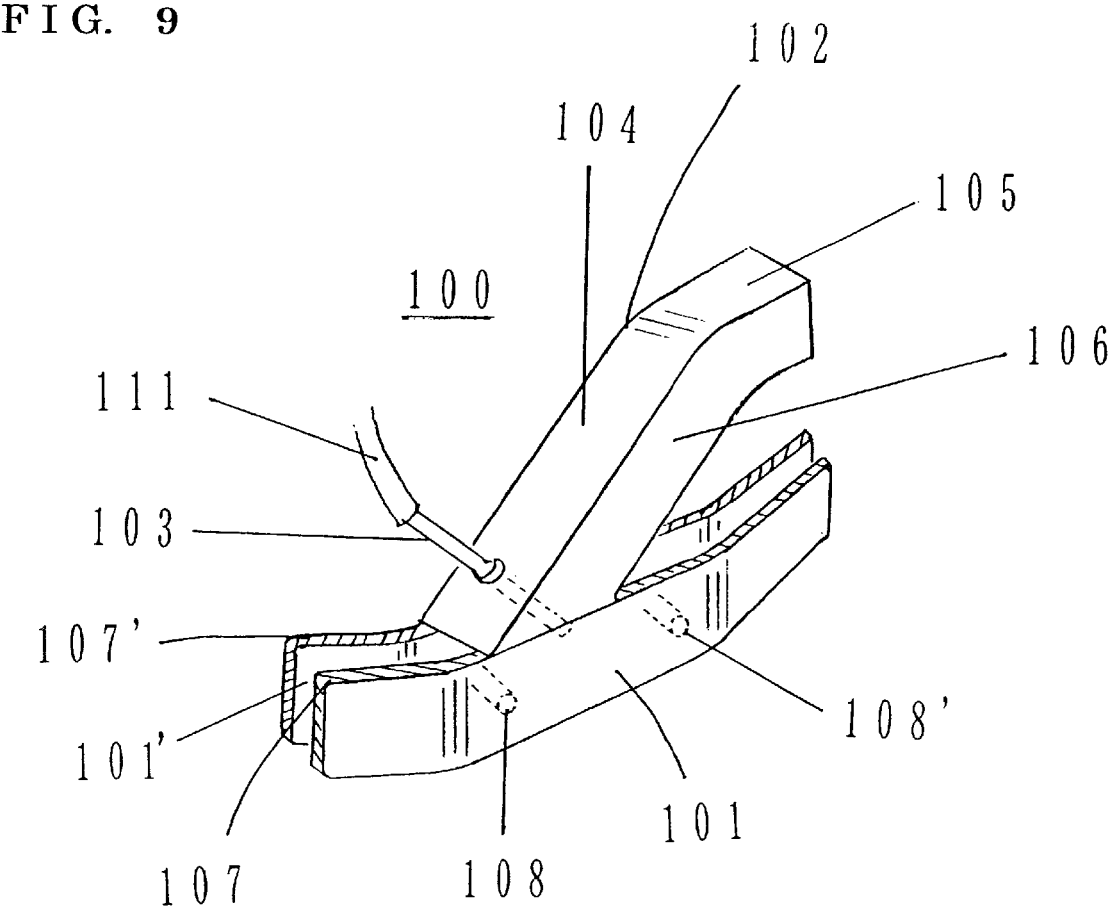
FIG. 9 is a perspective view of a gas discharge device.
Figure 10:
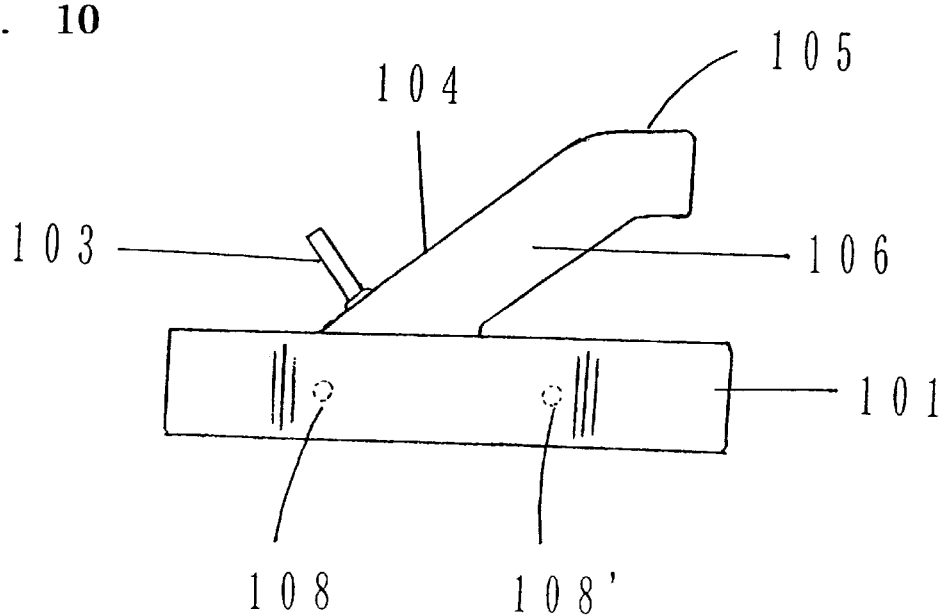
FIG. 10 is a side view of the gas discharge device of FIG. 9.

This gas discharge device 200 is different from the structure of the gas discharge device 100 illustrated in FIG. 9 in that one rectangular base plate 201 out of the opposed rectangular base plates 201, 201' is shorter than the other rectangular base plate 201' and in that the front end portion and rear end portion of the rectangular base plate 201 are not bent, but is the same in the other respects. Numeral 202 designates the bubble guide member, 203 the discharge nozzle, 211 the gas inlet tube, 201 and 201' the rectangular base plates, 204 the inclined wall, 205 the upper wall, 206 the side wall, 207 and 207' the upper surfaces, and 208 and 208' the fixing members.

Weights (not illustrated) as the weight adjusting means are detachably attached to the rectangular base plates 201, 201'.

Figure 20:
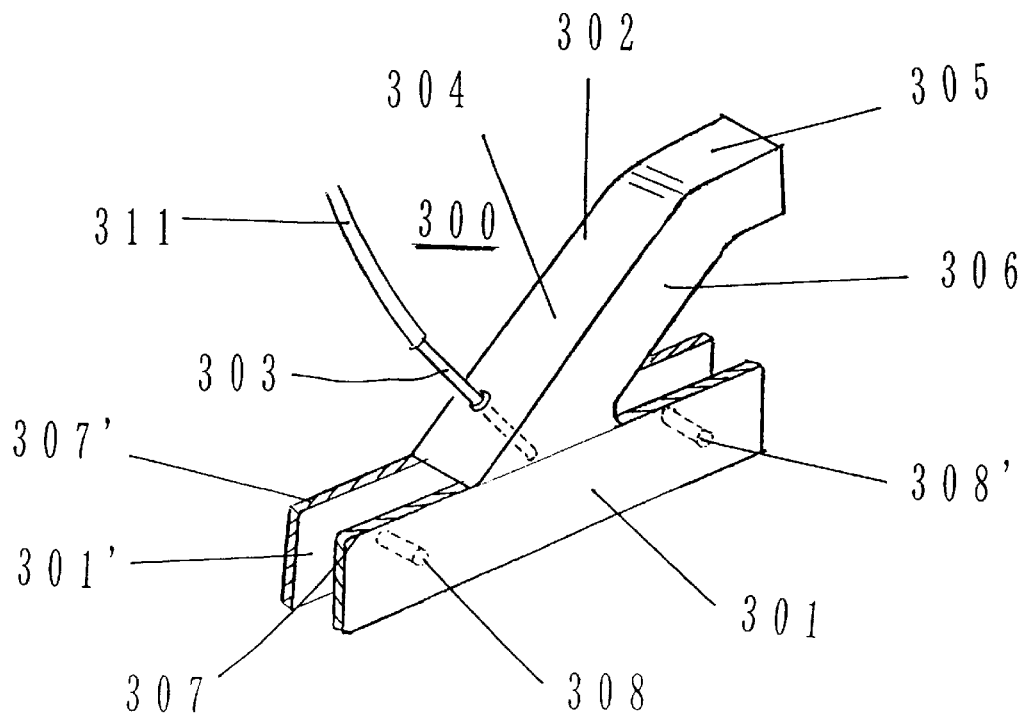
FIG. 20 is a perspective view to show a further example of the gas discharge device of the present invention.

FIG. 20 is a perspective view to show a further embodiment of the gas discharge device of the present invention.

This gas discharge device 300 is different from the structure of the gas discharge device 100 illustrated in FIG. 9 in that the front end and rear end of both the opposed rectangular base plates 301, 301' are not bent, but is the same in the other respects. Numeral 302 designates the bubble guide member, 303 the discharge nozzle, 311 the gas inlet tube, 301 and 301' the rectangular base plates, 304 the inclined wall, 305 the upper wall, 306 the side wall, 307 and 307' the upper surfaces of the rectangular base plates, and 308 and 308' the fixing members.

Weights (not illustrated) as the weight adjusting means are detachably attached to the rectangular base plates 301, 301'.

Figure 21:
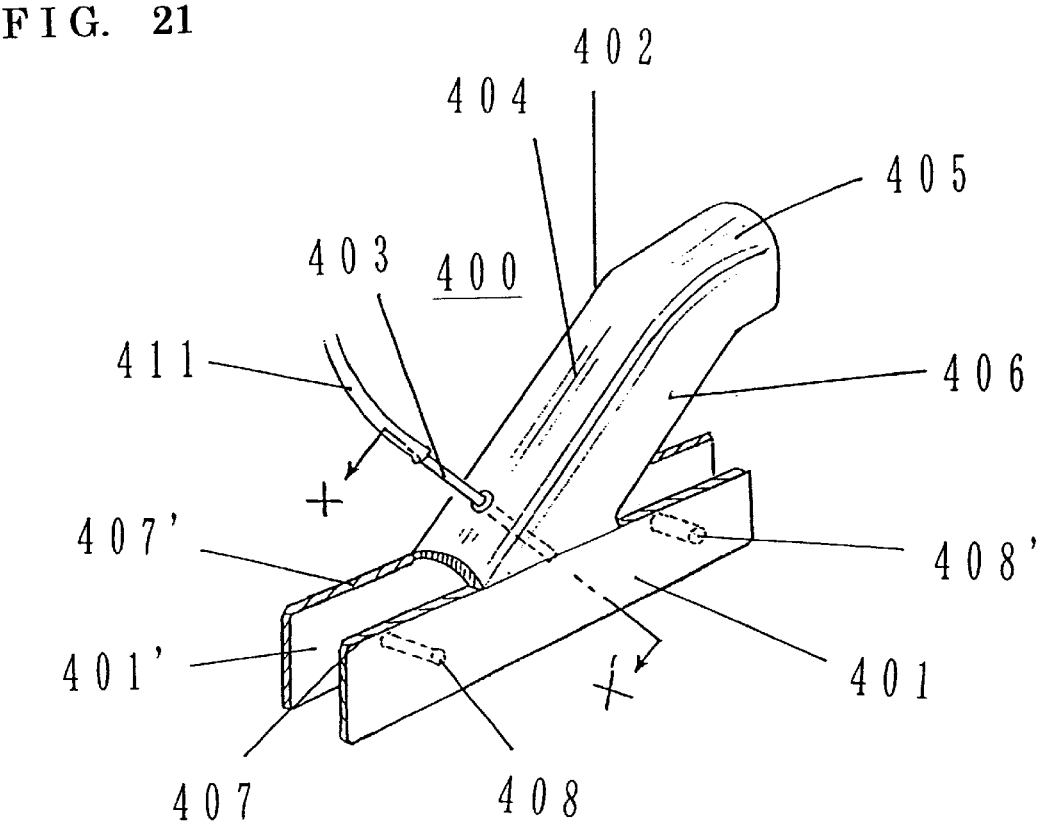
FIG. 21 is a perspective view to show yet another example of the gas discharge device of the present invention.
Figure 22:
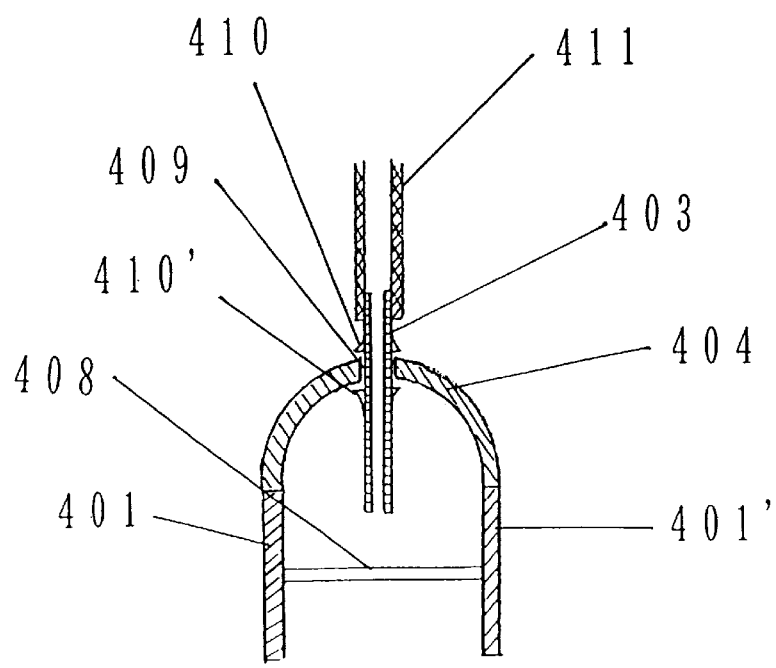
FIG. 22 is a sectional view along the line X–X' in FIG. 21.

FIG. 21 is a perspective view to show yet another embodiment of the gas discharge device of the present invention. FIG. 22 is a sectional view along the line X–X' of the gas discharge device in FIG. 21.

This gas discharge device 400 is comprised of the opposed rectangular base plates 401, 401', the bubble guide member 402 of a doglegged contour in the inverse-U-shaped cross section opening down, and the discharge nozzle 403 to which the gas inlet tube 411 is connected, the bubble guide member 402 being provided as inclined with respect to the upper surfaces 407, 407' of the rectangular base plate portions and having the structure of the inverse-U-shaped cross section in which the upper end of the semicircular inclined wall 404 as an upper surface extends to form an upper wall 405 as keeping the semicircular shape and being bent almost horizontally and in which the both side walls (comprised of side wall 406 and the other side wall (not illustrated)) hang down from the edges of the semicircular shape, the lower ends of the both side walls being joined to the upper surfaces 407, 407' of the rectangular base plates. The discharge nozzle 403 is set rotatably through the through hole 409 bored in the top part of the semicircular shape in the lower part of the inclined wall 404 of the bubble guide member 402 of the inverse-U-shaped cross section and two stoppers 410, 410' are located on the outer peripheral part of the discharge nozzle 403 at the opposed positions on either side of the through hole 409 so as to prevent the discharge nozzle from slipping off the through hole 409.

The end formed by the upper wall 405 and the both side walls is open and the rectangular base plates 401, 401' are fixed to each other by the fixing members 408, 408'.

In this embodiment the two rectangular base plates are not bent at the front end and at the rear end, but they may also be similarly used even if they have such structure that the front end portion and rear end portion of the two rectangular base plates are bent in the same direction or such structure that only one rectangular base plate is bent at the front end portion and/or at the rear end portion.

Weights (not illustrated) as the weight adjusting means are detachably attached to the rectangular base plates 401, 401'.

Industrial Application

As described above, the culture devices, the gas discharge devices, or the culture apparatus as a combination of the culture device with the gas discharge device according to the present invention are suitable for the culture in high concentrations of microalgae and the culture solution does not have to be mechanically agitated intentionally. Further, when the artificial light source is set in the inside space of the device, the 24-hour continuous culture can be effected outdoors, and in the indoor culture the light can be irradiated from the inside and outside of the device, so as to realize continuous culture.

What is claimed is:

1. A culture device of microalgae, said device being one of either shape selected from a domed shape, a conical shape, and a cylindrical shape, wherein the culture device of the domed shape comprises an outside semispherical dome of a transparent material, an inside semispherical dome of a transparent material, and a bottom portion connecting lower ends of the two domes, a cylindrical opening portion is provided at top part of the outside semispherical dome, and an introducing member of air and/or carbonic acid gas and a discharging member of a culture solution are provided in the bottom portion, wherein the culture device of the conical shape comprises an outside conical peripheral wall of a transparent material, a transparent inside conical peripheral wall, and a bottom portion connecting lower ends of the two peripheral walls, a cylindrical opening portion is provided at top part of the outside conical peripheral wall, and an introducing member of air and/or carbonic acid gas and a discharging member of a culture solution are provided in the bottom portion, or, wherein the culture device of the cylindrical shape comprises an outside cylindrical peripheral wall having an upper wall of a transparent material, an inside cylindrical peripheral wall having an upper wall a transparent material, and a bottom portion connecting lower ends of the two peripheral walls, a cylindrical opening portion is provided in central part of the upper wall of the outside cylindrical peripheral wall, and an introducing member of air and/or carbonic acid gas and a discharging member of a culture solution are provided in the bottom portion.

2. The culture device according to claim 1, wherein the shape of the culture device is the domed shape.

3. The culture device according to claim 1, wherein the shape of the culture device is the conical shape.

4. The culture device according to claim 1, wherein the shape of the culture device is the cylindrical shape.

5. The culture device according to claim 1, wherein the transparent material is acrylic resin.

6. The culture device according to claim 1, wherein a member for water sprinkling is further provided outside the cylindrical opening portion and a sprinkled water receiver is further provided around the outside periphery of the bottom portion.

7. The culture device according to claim 1, wherein an artificial light source is further provided in an inside space of the inside semispherical dome, the inside conical peripheral wall, or the inside cylindrical peripheral wall.

8. A gas discharge device for use in a culture device of microalgae, the gas discharge device comprising two opposed rectangular base plates, a bubble guide member of a ⊓-shaped cross section opening down, and a discharge nozzle, wherein the bubble guide member is set as inclined with respect to upper surfaces of the rectangular base plates, an inclined wall as an upper surface of the bubble guide member is bent at an upper end thereof to form an upper wall extending substantially horizontally, the bubble guide member has side walls hanging down from both side edges of the inclined wall and the upper wall, lower ends of the both side walls are joined to the upper surfaces of the rectangular base plates, and the discharge nozzle is rotatably mounted through a through hole bored in a lower portion of the inclined wall.

9. A gas discharge device for use in a culture device, comprising two opposed rectangular base plates, a bubble guide member of an inverse-U-shaped cross section opening down, and a discharge nozzle, wherein the bubble guide member is set as inclined with respect to upper surfaces of the rectangular base plates, an upper end of a semicircular inclined wall as an upper surface of the bubble guide member is bent to form an upper wall extending substantially horizontally as keeping the semicircular shape, the bubble guide member has side walls hanging down from both side edges of the inclined wall and the upper wall, lower ends of the both side walls are joined to the upper surfaces of the rectangular base plates, and the discharge nozzle is rotatably mounted through a through hole bored in a lower portion of the inclined wall.

10. The gas discharge device selected from claim 8 or 9, wherein at least one of the two opposed rectangular base plates is bent in the same direction at a front end portion and/or at a rear end portion.

11. The gas discharge device selected from claim 8 or 9, wherein at least one of the two opposed rectangular base plates is provided with weight adjusting means.

12. A microalgae culture apparatus comprising a culture device body and a gas discharge device, wherein the culture device body is a culture device of a domed shape, a conical shape, or a cylindrical shape, wherein the culture device of the domed shape comprises an outside semispherical dome of a transparent material, an inside semispherical dome of a transparent material, and a bottom portion connecting lower ends of the two domes, a cylindrical opening portion is provided at top part of the outside semispherical dome, and a discharging member of a culture solution are provided in the bottom portion, wherein the culture device of the conical shape comprises an outside conical peripheral wall of a transparent material, a transparent inside conical peripheral wall, and a bottom portion connecting lower ends of the two peripheral walls, a cylindrical opening portion is provided at top part of the outside conical peripheral wall, and a discharging member of a culture solution are provided in the bottom portion, or, wherein the culture device of the cylindrical shape comprises an outside cylindrical peripheral wall having an upper wall of a transparent material, an inside cylindrical peripheral wall having an upper wall of a transparent material, and a bottom portion connecting lower ends of the two peripheral walls, a cylindrical opening portion is provided in central part of the upper wall of the outside cylindrical peripheral wall, and a discharging member of a culture solution are provided in the bottom portion, wherein the gas discharge device comprises two opposed rectangular base plates, a bubble guide member of a ⊓-shaped cross section or an inverse-U-shaped cross section opening down, and a discharge nozzle, the bubble guide member is set as inclined with respect to upper surfaces of the rectangular base plates, an inclined wall as an upper surface of the bubble guide member is bent at an upper end thereof to form an upper wall extending substantially horizontally, the bubble guide member has side walls hanging down from both side edges of the inclined wall and the upper wall, lower ends of the both side walls are joined respectively to the two upper surfaces of the rectangular base plates, and the discharge nozzle is rotatably mounted through a through hole bored in a lower portion of the inclined wall.

13. The culture apparatus according to claim 12, wherein the transparent material of the culture device body is acrylic resin.

14. The culture apparatus according to claim 12, wherein an introducing member of air and/or carbonic acid gas is further provided in the bottom portion of the culture device body.

15. The culture apparatus according to claim 12, wherein the culture device body further comprises a water sprinkling member outside the cylindrical opening portion and a sprinkled water receiver around the outside periphery of the bottom portion.

16. The culture apparatus according to claim 12, wherein the culture device body further comprises an artificial light source in an inside space of the inside semispherical dome, the inside conical peripheral wall, or the inside cylindrical peripheral wall.

17. The culture apparatus according to claim 12, wherein at least one of the rectangular base plates of the gas discharge device is bent in the same direction at a front end portion and/or at a rear end portion.

18. The culture apparatus according to claim 12, wherein at least one of the two rectangular base plates of the gas discharge device is provided with weight adjusting means.

* * * * *